United States Patent

(12) United States Patent
Po et al.

(10) Patent No.: US 11,807,645 B2
(45) Date of Patent: Nov. 7, 2023

(54) POLYMERS CONTAINING INDACEN-4-ONE DERIVATIVES

(71) Applicant: Eni S.p.A., Rome (IT)

(72) Inventors: Riccardo Po, Leghorn (IT); Gabriele Bianchi, Novara (IT)

(73) Assignee: Eni S.P.A., Rome (IT)

( * ) Notice: Subject to any disclaimer, the term of this patent is extended or adjusted under 35 U.S.C. 154(b) by 535 days.

(21) Appl. No.: 16/989,030

(22) Filed: Aug. 10, 2020

(65) Prior Publication Data

US 2021/0040110 A1 Feb. 11, 2021

Related U.S. Application Data

(62) Division of application No. 15/573,865, filed as application No. PCT/EP2016/060935 on May 16, 2016, now Pat. No. 10,870,655.

(30) Foreign Application Priority Data

May 14, 2015 (IT) .............................. MI2015A0676

(51) Int. Cl.
*C07D 495/04* (2006.01)
*H10K 85/10* (2023.01)
(Continued)

(52) U.S. Cl.
CPC ......... *C07D 495/04* (2013.01); *C08G 61/124* (2013.01); *C08G 61/126* (2013.01);
(Continued)

(58) Field of Classification Search
CPC .... C08G 2261/3243; C08G 2261/3246; C08G 61/126; C08G 2261/414; C08G 2261/91;
(Continued)

(56) References Cited

U.S. PATENT DOCUMENTS

2014/0021448 A1 1/2014 Polander et al.
2014/0151680 A1 6/2014 Terai et al.
(Continued)

FOREIGN PATENT DOCUMENTS

JP     20130193965 A    9/2013
JP     201431364   *    2/2014   .......... C07D 495/04
(Continued)

OTHER PUBLICATIONS

International Search Report for PCT/EP2016/060935, dated Jun. 29, 2016, 12 pages.
(Continued)

*Primary Examiner* — Shane Fang
(74) *Attorney, Agent, or Firm* — Praedcere Law

(57) ABSTRACT

Polymer comprising an indacen-4-one derivative, said polymer having general formula (IX), (X) or (XI):

(IX)

(X)

(Continued)

-continued

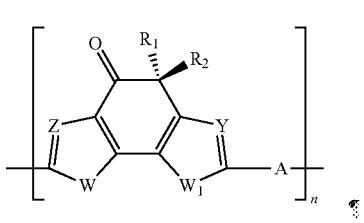

(XI)

in which:
W and $W_1$, Z and Y, $R_1$ and $R_2$, are as described;
D represents an electron-donor group;
A represents an electron-acceptor group;
n is an integer ranging from 10 to 500.

2 Claims, 7 Drawing Sheets

(51) Int. Cl.
*C08G 61/12* (2006.01)
*H10K 30/30* (2023.01)
*H10K 85/20* (2023.01)

(52) U.S. Cl.
CPC ........ *H10K 85/113* (2023.02); *C08G 2261/11* (2013.01); *C08G 2261/122* (2013.01); *C08G 2261/1412* (2013.01); *C08G 2261/1424* (2013.01); *C08G 2261/3223* (2013.01); *C08G 2261/3243* (2013.01); *C08G 2261/3246* (2013.01); *C08G 2261/514* (2013.01); *C08G 2261/91* (2013.01); *H10K 30/30* (2023.02); *H10K 85/215* (2023.02); *Y02E 10/549* (2013.01); *Y02P 70/50* (2015.11)

(58) Field of Classification Search
CPC .............. C07D 417/14; H01L 51/0043; H01L 51/0036; H01L 51/0047; H01L 51/4253; Y02E 10/549
See application file for complete search history.

(56) References Cited

U.S. PATENT DOCUMENTS

| | | | | |
|---|---|---|---|---|
| 2015/0144200 A1* | 5/2015 | Iketaki | ................... | H10K 30/81 252/500 |
| 2015/0128891 A1 | 9/2015 | Hodebourg | | |
| 2015/0353583 A1* | 12/2015 | Ohya | ................... | C08G 61/126 528/380 |

FOREIGN PATENT DOCUMENTS

| | | | | |
|---|---|---|---|---|
| JP | 2014019781 | * | 2/2014 | ........... Y02E 10/549 |
| JP | 2014019781 A | | 2/2014 | |
| JP | 2014031364 A | | 2/2014 | |
| WO | WO2011156478 A2 | | 12/2011 | |
| WO | WO 2013183549 | * | 12/2013 | ............. B82Y 10/00 |
| WO | WO2013184549 A1 | | 12/2013 | |
| WO | WO20150128891 A1 | | 9/2015 | |

OTHER PUBLICATIONS

Keshtov et al, "New narrow-band-gap conjugated copolymers based on benzodithiophene: Synthesis and photovoltaic properties", Polymer Science Series B, vol. 56, No. 1, 2014, pp. 89-108.

Huo et al, "Synthesis of a polythienol3,4-b]thiophene derivative with a low-lying HOMO level and its application in polymer solar cells", Chemical Communication, 2011, vol. 47, pp. 8850-8852.

Yu et al, "How to design low bandgap polymers for highly efficient organic solar cells", Materials Today, vol. 17, No. 1, 2014, pp. 11-15.

You et al, "Structure-Property Optimizations in Donor Polymers Via Electronics, Substituents, and Side Chains Toward High Efficiency Solar Cells", Macromolecular Rapid Communications, vol. 33, 2012, pp. 1162-1177.

Havinga et al, "A new class of small band-gap organic polymer conductors", Polymer Bulletin, vol. 29, 1992, pp. 119-126.

Chen et al, "Development of Novel Conjugated Donor Polymers for High-Efficiency Bulk-Heter Function Photovoltaic Devices", Account of Chemical Research, vol. 42 (11), 2009, pp. 1709-1718.

Kanbara et al, "The effect of a solvent on direct arylation polycondensation of substituted thiopenes", Polymer Chemistry, vol. 6, 2015, pp. 891-895.

Ozawa et al, "A Highly Efficient Catalyst for the Synthesis of Alternating Copolymers with Thieno[3,4-c] Pyrrole-4,6-dione Units via Direct Arylation Polymerization", Macromolecules, vol. 47, 2014, pp. 626-631.

1st Office Action for Chinese patent application 201680027906X, dated Nov. 21, 2019, 7 pages (English translation provided).

Amsalu et al, "Synthesis and characterization of dithieno benzothiadiazole-based donor-acceptor conjugated polymers for organic solar cell applications", Tetrahedron Letters, 55, 2014, pp. 4849-4852.

Hussain et al, "Design and Synthesis of ERa/ERB selective coumarin and chromene derivatives as potential anti-breast cancer and anti-osteoporotic agents", RSC Advances, 4(17), 2014, pp. 8828-8845.

Office Action dated Mar. 6, 2020 in U.S. Appl. No. 15/573,865, 13 pages.

* cited by examiner

1: inverted polymer solar cell;

2: ITO (Indium Tin Oxide);

3: zinc oxide (ZnO);

4: active layer;

5: molybdenum oxide (MoO$_3$);

6. silver (Ag);

7. glass.

1: conventional polymer solar cell;

2: ITO (Indium Tin Oxide);

3: PEDOT:PSS [poly(3,4-ethylenedioxythiophene)poly(styrenesulfonate];

4: active layer;

5: aluminium;

6. glass.

POLYMERS CONTAINING INDACEN-4-ONE DERIVATIVES

The present invention relates to an indacen-4-one derivative.

More particularly the present invention relates to an indacen-4-one derivative containing heteroatoms.

The present invention also relates to a process for preparation of said indacen-4-one derivative through a multistage process described below.

Said indacen-4-one derivative may advantageously be used in the synthesis of electron-donor polymers, said polymers being a further object of the present invention.

As a consequence, the present invention also relates to a polymer comprising an indacen-4-one derivative, said polymer having general formula (IX), (X) or (XI), reported below.

Said polymer may advantageously be used in the construction of photovoltaic devices (or solar devices) such as for example photovoltaic cells (or solar cells), photovoltaic modules (or solar modules), on either a rigid or flexible support.

Photovoltaic devices (or solar devices) are devices capable of converting the energy of light radiation into electrical energy. At the present time, most photovoltaic devices (or solar devices) which may be used for practical applications, make use of the chemical and physical properties of photoactive materials of an inorganic type, in particular high purity crystalline silicon. Because of the high costs of producing the silicon scientific research, however, has long been orienting its efforts to the development of alternative materials of an organic type having a conjugated oligomer or polymer structure with the aim of obtaining organic photovoltaic devices (or solar devices) such as, for example, organic photovoltaic cells (or solar cells). In fact, unlike high purity crystalline silicon, said materials of an organic type are characterised by relative ease of synthesis, low production cost, low weight in the corresponding organic photovoltaic devices (or solar devices), and also allow said materials of an organic type to be recycled at the end of the life cycle of the organic photovoltaic device (or solar device) in which they are used.

The abovementioned advantages make use of said materials of an organic type energetically and economically attractive, despite possible lower efficiencies (η) in the organic photovoltaic devices (or solar devices) so obtained in comparison with inorganic photovoltaic devices (or solar devices).

The functioning of organic photovoltaic devices (or solar devices) such as, for example, organic photovoltaic cells (or solar cells), is based on the combined use of an electron-acceptor compound and an electron-donor compound. In the state of the art the most widely used electron-acceptor compounds in organic photovoltaic devices (or solar devices) are fullerene derivatives, in particular PC61BM (6,6-phenyl-$C_{61}$-methyl butyric ester) or PC71BM (6,6-phenyl-$C_{71}$-methyl butyric ester), which have yielded greater efficiencies when mixed with electron-donor compounds selected from π-conjugated polymers such as for example polythiophenes (η>5%), polycarbazoles (η>6%), poly(thienothiophene)benzodithiophene derivatives (PTB) (η>8%).

It is known that the elemental process of converting light into electrical current in an organic photovoltaic cell (or solar cell) takes place through the following stages:

1. absorption of a photon by the electron-donor compound with the formation of an excitone, that is a pair of "electron-electronic gap (or hole)" charge transporter;
2. diffusion of the excitone in a region of the electron-donor compound up to the interface with the electron-acceptor compound;
3. dissociation of the excitone into two charge transporters: electron (−) in the accepting phase (i.e. in the electron-acceptor compound) and electronic gap [(or hole) (+)] in the donor phase (i.e. in the electron-donor compound);
4. transport of the charges so formed to the cathode (electron via the electron-acceptor compound) and to the anode [electronic gap (or hole) via the electron-donor compound], with the generation of an electrical current in the circuit of the organic photovoltaic cell (or solar cell).

The process of photoabsorption with formation of the excitone and subsequent transfer of the electron to the electron-acceptor compound comprises the excitation of an electron from the HOMO ("Highest Occupied Molecular Orbital") to the LUMO ("Lowest Unoccupied Molecular Orbital") of the electron-donor compound and, subsequently, the passage from the latter to the LUMO of the electron-acceptor compound.

Because the efficiency of an organic photovoltaic cell (or solar cell) depends on the number of free electrons which are generated through disassociation of the excitones, which may in turn be directly correlated to the number of photons absorbed, one of the structural characteristics of the electron-donor compounds which has the greatest effect on such efficiency is the difference in energy between the HOMO and LUMO orbitals of the electron-donor compound, that is the so-called "band-gap". The maximum wavelength value at which the electron-donor compound is capable of effectively collecting and converting photons into electrical energy, that is the process known as "light harvesting" or "photon harvesting", depends on this difference, in particular. In order to obtain acceptable electrical currents, the "band-gap", that is the difference in energy between the HOMO and LUMO of the donor compound, should not on the one hand be too high so that the greatest number of photons may be absorbed, but should not on the other hand be too low, because this might reduce the voltage at the electrodes of the device.

In the simplest manner of operation, organic photovoltaic cells (or solar cells) are manufactured by introducing a thin layer (approximately 100 nanometres) of a mixture of the electron-acceptor compound and the electron-donor compound between two electrodes usually consisting of indium-tin oxide (ITO) (anode) and aluminium (Al) (cathode) (an architecture known as "bulk heterojunction"). Generally, in order to produce a layer of this type, a solution of the two compounds is prepared and then a photoactive film is created on the anode [indium-tin oxide (ITO)] starting from said solution, using suitable deposition techniques such as, for example, spin coating, spray-coating, ink-jet printing, and the like. Finally, the opposite electrode [i.e. the aluminium (Al) cathode] is deposited on the dried film. Optionally, other additional layers capable of performing specific functions of an electrical, optical, or mechanical nature, may be introduced between the electrodes and the photoactive film.

In general, in order to encourage the electronic gaps (or holes) to reach the anode [indium-tin oxide (ITO)] and at the same time to block electron transport, thus improving charge harvesting by the electrode and inhibiting recombination phenomena, before the photoactive film is created from the mixture of acceptor compound and donor compound as described above, a film starting from an aqueous suspension of PEDOT:PSS [poly(3,4-ethylene dioxide thiophene)polystyrene sulfonate] is deposited, using suitable deposition techniques such as, for example, spin-coating, spray-coating, ink-jet printing, and the like. The electron-donor compound most commonly used in the construction of organic photovoltaic cells (or solar cells) is regioregular poly(3-hexylthiophene) (P3HT). This polymer has optimum electronic and optical characteristics (good values for the HOMO and LUMO orbitals, a good polar absorption coefficient), good solubility in the solvents which are used to manufacture photovoltaic cells (or solar cells), and discrete mobility for the electronic gap.

Other examples of polymers which may advantageously be used as electron-donor compounds are: PCDTBT polymer {poly[N-9"-heptadecanyl-2,7-carbazole-alt-5,5-(4',7'-di-2-thienyl-2',1',3'-benzothiadiazole]}, PCPDTBT polymer {poly[2,6-(4,4-bis-(2-ethylhexyl)-4H-cyclopenta[2,1-b;3,4-b']-dithiophene)-alt-4,7-(2,1,3-benzothiadiazole)]}.

Electron-donor compounds containing benzodithiophenyl units which have a similar structure to poly(3-hexylthiophene) (P3HT), in which however the thiophene units are planarised by means of benzene rings, are also known. In addition to reducing the oxidation potential of said electron-donor compounds, this characteristic improves their stability in air and ensures that they pack readily and, as a consequence, have a high molecular order during production of the photoactive film: this is reflected in excellent charge transport properties [electrons or electronic gaps (holes)]. As a consequence higher performance photovoltaic devices may be produced through the use of electron-donor compounds containing benzodithiophenyl units.

For example, electron-donor compounds containing benzodithiophene units are described by Huo L. et al. in the article: "Synthesis of a polythieno[3,4-b]thiophene derivative with a low-lying HOMO level and its application in polymer solar cells", "*Chemical Communication*" (2011), Vol. 47, pg. 8850-8852. Said article describes the preparation of a polythieno[3,4-b]thiophene derivative by copolymerisation between a planar benzodithiophene having a low HOMO value and a thieno[3,4-b]thiophenyl unit.

It is known that benzodithiophene and/or its isomers [e.g., benzo[1,2-b:4,5-b]dithiophene, or (BDT), and benzo[2,1-b:3,4-b]dithiophene, or (BDP)] are compounds of significant interest whose synthesis has been the subject of several researches.

Generally, the electron-donor materials used in high efficiency photovoltaic cells are almost exclusively represented by polymers in which an electron-rich unit alternates with an electron-poor unit. Further details relating to said polymers can, for example, be found in the following articles: Yu L. et al., "How to design low bandgap polymers for highly efficient organic solar cells", "*Materials Today*" (2014), Vol. 17, No. 1, pg. 11-15; You W. et al., "Structure-Property Optimizations in Donor Polymers via Electronics, Substituents, and Side Chains Toward High Efficiency Solar Cells", "*Macromolecular Rapid Communications*" (2012), Vol. 33, pg. 1162-1177; Havinga E. E. et al., "A new class of small band-gap organic polymer conductors", "*Polymer Bulletin*" (1992), Vol. 29, pg. 119-126.

However, said electron-donor polymers have not always proved to be the best. In fact, because the flow of solar radiation photons reaching the surface of the earth is a maximum for energy values around 1.8 eV (corresponding to radiation having a wavelength of approximately 700 nm), the process known as "light harvesting" or "photon harvesting" is not very efficient because of the high band-gap values (generally more than 2 eV-3 eV) characterising many of the abovementioned electron-donor polymers, and only part of the overall solar radiation is converted into electrical energy.

In order to improve the yield of the process known as "light harvesting" or "photon harvesting" and, consequently, the efficiency of organic photovoltaic devices (or solar devices) it is therefore essential to identify new electron-donor polymers capable of capturing and converting the solar radiation wavelengths having the lowest energy, that is electron-donor polymers characterised by band-gap values lower than those of the polymers typically used as electron-donors.

Efforts have therefore been made in the art to identify electron-donor polymers having a low band-gap value (i.e. a band-gap value of less than 2 eV).

For example, one of the strategies most commonly used to obtain electron-donor polymers having a low band-gap value is to synthesise alternating conjugated polymers comprising electron-rich (donor) and electron-poor (acceptor) units. A synthesis of said type is for example described by Chen J. et al. in the article "Development of Novel Conjugated Donor Polymers for High-Efficiency Bulk-Heterojunction Photovoltaic Devices", "*Account of Chemical Research*" (2009), Vol. 42(11), pg. 1709-1718.

Generally, processes for preparation of the aforesaid alternating conjugated polymers provide for the use of two monomers, i.e. an electron-rich monomer (T rich) and an electron-poor monomer (T poor), suitably and selectively provided with functional groups, which react together to form the final polymer. The synthesis strategy therefore provides for two separate multistage routes of synthesis (synthesis of the electron-rich monomer and synthesis of the electron-poor monomer), which may also be very complex and comprise various stages (for example, up to 22 stages) before the desired polymer is obtained. The final stage generally provides for a polymerisation reaction (in particular, in the case of high efficiency polymers) based on the "cross-coupling" reaction catalysed by palladium complexes, working in accordance with a Stille reaction diagram shown in FIG. 6 in which R, which may be the same or different, represent a linear or branched $C_1$-$C_{20}$ alkyl group or a Suzuki reaction diagram shown in FIG. 7 in which R, which are the same or different, represent a hydrogen atom, or a linear or branched $C_1$-$C_{20}$ alkyl group, or the OR groups together with other atoms to which they are linked may form a heterocyclic ring having the following formula:

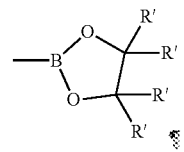

in which the R' substituents, which are the same or different, represent a hydrogen atom, or a linear or branched $C_1$-$C_{20}$ alkyl group, and B is boron.

Generally, the abovementioned Stille and Suzuki reactions are catalyst by bis(triphenylphosphine)palladium (II) chloride [$PdCl_2(PPh_3)_2$], as such or prepared in situ from palladium chloride ($PdCl_2$) and triphenylphosphine, or from palladium(0)-tetrakistriphenylphosphine [$Pd(PPh_3)_3$], or from palladium(II)acetate [Pd(OAc)$_2$], or from other phosphines such as, for example, tri-ortho-tolyl phosphine or tri-para-tolyl phosphine.

The Stille and Suzuki reactions may be carried out in solvents selected, for example, from ethers (for example, 1,2-dimethoxyethane, 1,4-dioxane, tetrahydrofuran); hydrocarbons (for example, toluene, xylene); dipolar aprotic solvents [for example, N,N-dimethylformamide (DMF), N-methyl-2-pyrrolidone (NMP), dimethylsulfoxide (DMSO)]. Generally, the reaction temperatures are ranging from 80° C. to 160° C.

In the case of the Suzuki reaction a saturated aqueous solution of sodium bicarbonate or of potassium bicarbonate, or a saturated aqueous solution of sodium carbonate or potassium carbonate, has to be added.

Generally, the product obtained at the end of the aforesaid reactions, i.e. the polymer, is precipitated in alcohol such as, for example, methanol, the precipitate obtained is washed with a solvent such as, for example, heptane or ethyl ether, obtaining a residue which is redissolved in a solvent such as, for example, chloroform or chlorobenzene and reprecipitated in alcohol such as, for example, methanol.

Nevertheless, the processes described above may show some disadvantages.

For example, in the case of the Stille reaction diagram (FIG. 6), the stannylate compounds used in the reaction cannot be easily purified using normal laboratory techniques. As a consequence, low yields of stannylate compounds are obtained because significant quantities of the same are lost during purification. Moreover, the processes reported in the abovementioned diagrams require the use of highly flammable and hazardous substances such as, for example, lithium alkyls, and perfectly anhydrous working conditions. Furthermore, the organic tin derivatives are substances that are highly toxic to man and harmful to the environment.

In the case of the Suzuki reaction diagram (FIG. 7), the corresponding acid or ester boron derivatives are used, instead of boron derivatives. However, also boron derivatives may show some disadvantages. Even in this case their purification is not, in fact, simple and it is often accompanied by partial degradation of the boron derivative.

Unlike stannylate compounds, boron esters are not substances that are toxic and harmful to the environment. However, like the stannylate compounds their preparation requires the use of highly flammable and hazardous substances such as lithium alkyls, and perfectly anhydrous working conditions.

Moreover, the study of new electron-donor compounds and/or of new polymers having a low band-gap value (i.e. a band-gap value of less than 2 eV) is still of great interest. The Applicant has therefore set itself the problem of finding a compound capable of being used as a monomer unit in the synthesis of electron-donor polymers which may in turn be used in the construction of photovoltaic devices (or solar devices) and capable of overcoming the abovementioned disadvantages.

The Applicant has now found an indacen-4-one derivative which may advantageously be used as a monomer unit in the synthesis of electron-donor polymers having a low band-gap value (i.e. a band-gap value of less than 2 eV) which may in turn be used in the construction of photovoltaic devices (or solar devices).

An object of the present invention therefore relates to an indacen-4-one derivative having general formula (I):

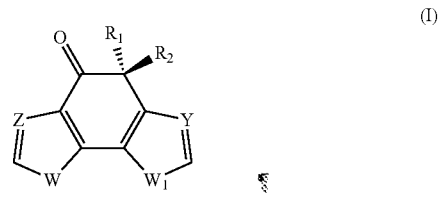

(I)

in which:
W and W$_1$, which are the same or different, preferably the same, represent an oxygen atom; a sulfur atom; an N—R$_3$ group in which R$_3$ represents a hydrogen atom, or is selected from linear or branched C$_1$-C$_{20}$, preferably C$_2$-C$_{10}$, alkyl groups;

Z and Y, which are the same or different, preferably the same, represent a nitrogen atom; or a C—R$_4$ group in which R$_4$ represents a hydrogen atom, or is selected from linear or branched C$_1$-C$_{20}$, preferably C$_2$-C$_{10}$, alkyl groups, optionally substituted cycloalkyl groups, optionally substituted aryl groups, optionally substituted heteroaryl groups, linear or branched C$_1$-C$_{20}$, preferably C$_2$-C$_{10}$, alkoxyl groups, R$_5$—O—[CH$_2$—CH$_2$—O]$_n$— polyethyleneoxyl groups in which R$_5$ is selected from linear or branched C$_1$-C$_{20}$, preferably C$_2$-C$_{10}$, alkyl groups, and n is an integer ranging from 1 to 4, —R$_6$—OR$_7$ groups in which R$_6$ is selected from linear or branched C$_1$-C$_{20}$, preferably C$_2$-C$_{10}$, alkylene groups and R$_7$ represents a hydrogen atom or is selected from linear or branched C$_1$-C$_{20}$, preferably C$_2$-C$_{10}$, alkyl groups, or is selected from R$_5$—[—OCH$_2$—CH$_2$—]$_n$— polyethyleneoxyl groups in which R$_5$ has the same meanings as above reported and n is an integer ranging from 1 to 4, —COR$_8$ groups in which R$_8$ is selected from linear or branched C$_1$-C$_{20}$, preferably C$_2$-C$_{10}$, alkyl groups, —COOR$_9$ groups in which R$_9$ is selected from linear or branched C$_1$-C$_{20}$, preferably C$_2$-C$_{10}$, alkyl groups; or represent a —CHO group, or a cyano group (—CN);

R$_1$ and R$_2$, which are the same or different, preferably the same, are selected from linear or branched C$_1$-C$_{20}$, preferably C$_2$-C$_{10}$, alkyl groups; optionally substituted cycloalkyl groups; optionally substituted aryl groups; optionally substituted heteroaryl groups; linear or branched C$_1$-C$_{20}$, preferably C$_2$-C$_{10}$, alkoxyl groups; R$_5$—O—[CH$_2$—CH$_2$—O]$_n$— polyethyleneoxyl groups in which R$_5$ has the same meanings as above reported and n is an integer ranging from 1 to 4; —R$_6$—OR$_7$ groups in which R$_6$ and R$_7$ have the same meanings as above reported; —COR$_8$ groups in which R$_8$ has the same meanings as above reported; —COOR$_9$ groups in which R$_9$ has the same meanings as above reported; or represent a —CHO group, or a cyano group (—CN).

In accordance with a preferred embodiment of the present invention, in said general formula (I):
W and W$_1$, which are the same, represent a sulfur atom;
Z and Y, which are the same, represent a C—R$_4$ group in which R$_4$ represents a hydrogen atom;
R$_1$ and R$_2$, which are the same, represent a C$_1$-C$_{20}$ alkyl group, preferably are an n-octyl group.

The present invention also relates to a process for the preparation of an indacen-4-one derivative having general formula (I). Said process makes it possible to avoid using stannylate or boronate compounds, with a consequent saving in process times and costs, as well as adverse effects on the environment and/or the health of operators. Moreover, said process makes it possible to reduce the quantity of metal residues present in the copolymers obtained, as well as to obtain tin-free copolymers.

A further object of the present invention is therefore a process for the preparation of an indacen-4-one derivative having general formula (I):

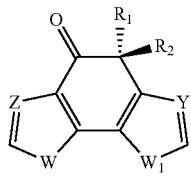

(I)

in which W, W₁, Z, Y, R₁ and R₂ have the same meanings as above reported, comprising the following stages:

(a) causing at least one heteroaryl compound incorporating a terminal alkyne group having general formula (II)

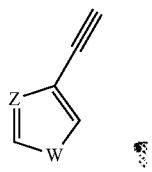

(II)

in which W and Z have the same meanings as above reported, to react with at least one heteroaryl halogenated compound having general formula (III)

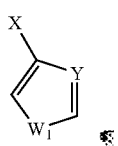

(III)

in which W₁ and Y have the same meanings as above reported and X represents a halogen atom selected from chlorine, bromine, iodine, preferably bromine, to obtain a compound having general formula (IV):

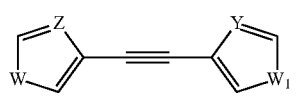

(IV)

in which W, Z, W₁ and Y have the same meanings as above reported;

(b) causing at least one compound having general formula (IV) obtained in stage (a) to react in the presence of at least one palladium-containing catalyst and of at least one copper-containing catalyst to obtain a compound having general formula (V):

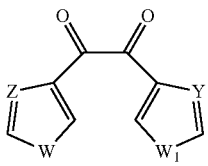

(V)

in which W, Z, W₁ and Y have the same meanings as above reported;

(c) causing at least one compound having general formula (V) obtained in stage (b) to react with at least one iron salt to obtain a compound having general formula (VI):

(VI)

in which W, Z, W₁ and Y have the same meanings as above reported;

(d) causing at least one compound having general formula (VI) obtained in stage (c) to react with at least one alkyl-magnesium bromide having general formula (VII):

R—MgBr    (VII)

in which R represents a linear or branched $C_1$-$C_{20}$ alkyl group, to obtain a compound having general formula (VIII):

(VIII)

in which R, W, Z, W₁ and Y have the same meanings as above reported;

(e) causing at least one compound having general formula (VIII) obtained in stage (d) to react with at least one strong organic acid, to obtain an indacen-4-one derivative having general formula (I).

For the purpose of the present description and of the following claims the definitions of numerical intervals will always include the extremes unless specified otherwise.

For the purpose of the present and of the following claims the term "comprising" also includes the terms "which essentially consists of" or "which consists of".

By the term "$C_1$-$C_{20}$ alkyl groups" are meant linear or branched, saturated or unsaturated alkyl groups having from 1 to 20 carbon atoms. Specific examples of $C_1$-$C_{20}$ alkyl groups are: methyl, ethyl, n-propyl, iso-propyl, n-butyl, iso-butyl, t-butyl, pentyl, ethyl-hexyl, hexyl, heptyl, n-octyl, nonyl, decyl, dodecyl.

By the term "cycloalkyl groups" are meant cycloalkyl groups having from 3 to 30 carbon atoms. Said cycloalkyl groups may optionally be substituted with one or more groups, which are the same or different, selected from halogen atoms such as, for example, fluorine, chlorine, bromine, preferably fluorine; hydroxyl groups, $C_1$-$C_{12}$ alkyl groups; $C_1$-$C_{12}$ alkoxyl groups; $C_1$-$C_{12}$ thioalkoxyl groups; $C_3$-$C_{24}$ tri-alkylsilyl groups; polyethyleneoxyl groups; cyano groups; amino groups; $C_1$-$C_{12}$ mono- or dialkylamine groups; nitro groups. Specific examples of cycloalkyl groups are: cyclopropyl, 2,2-difluorocyclopropyl, cyclobutyl, cyclopentyl, cyclohexyl, methylcyclohexyl, methoxycyclohexyl, fluorocyclohexyl, phenylcyclohexyl, decalin, abietyl.

By the term "aryl groups" are meant aromatic carbocyclic groups containing from 6 to 60 carbon atoms. Said aryl groups may optionally be substituted with one or more groups, which are the same or different, selected from halogen atoms such as, for example, fluorine, chlorine, bromine, preferably fluorine; hydroxyl groups, $C_1$-$C_{12}$ alkyl groups; $C_1$-$C_{12}$ alkoxyl groups; $C_1$-$C_{12}$ thioalkoxyl groups; $C_3$-$C_{24}$ tri-alkylsilyl groups; polyethyleneoxyl groups; cyano groups; amino groups; $C_1$-$C_{12}$ mono- or dialkylamine groups; nitro groups. Specific examples of aryl groups are: phenyl, methylphenyl, trimethylphenyl, methoxyphenyl, hydroxyphenyl, phenyloxyphenyl, fluorophenyl, pentofluorophenyl, fluorophenyl, bromophenyl, nitrophenyl, dimethylaminophenyl, naphthyl, phenylnaphthyl, phenanthrene, anthracene.

By the term "heteroaryl groups" are meant penta- or hexa-atom, aromatic heterocyclic groups, including benzo-condensates and heterobicyclic groups containing from 4 to 60 carbon atoms and from 1 to 4 hetero atoms selected from nitrogen, oxygen, sulfur, silicon, selenium, phosphorus. Said heteroaryl groups may optionally be substituted with one or more groups, which are the same or different, selected from halogen atoms such as, for example, fluorine, chlorine, bromine, preferably fluorine; hydroxyl groups, $C_1$-$C_{12}$ alkyl groups; $C_1$-$C_{12}$ alkoxyl groups; $C_1$-$C_{12}$ thioalkoxyl groups; $C_3$-$C_{24}$ tri-alkylsilyl groups; polyethyleneoxyl groups; cyano groups; amino groups; $C_1$-$C_{12}$ mono- or dialkylamine groups; nitro groups. Specific examples of heteroaryl groups are: pyridine, methylpyridine, methoxypyridine, phenylpyridine, fluoropyridine, pyrimidine, pyridazine, pyrazine, triazine, tetrazine, quinoline, quinoxaline, quinazoline, furan, thiophene, hexylthiophene, bromothiophene, dibromothiophene, pyrrole, oxazole, thiazole, isooxazole, isothiazol, oxadiazole, thiadiazole, pyrazole, imidazole, triazole, tetrazole, indole, benzofuran, benzothiophene, benzooxazole, benzothiazole, benzooxadiazole, benzothiadazole, benzopyrazole, benzomidazole, benzotriazole, triazolpyridine, triazolpyrimidine, coumarin. By the term "$C_1$-$C_{12}$ alkoxyl groups" are meant groups comprising an oxygen atom to which a linear or branched saturated or unsaturated $C_1$-$C_{20}$ alkyl group is linked. Specific examples of $C_1$-$C_{20}$ alkoxyl groups are: methoxyl, ethoxyl, n-propoxyl, iso-propoxyl, n-butoxyl, iso-butoxyl, t-butoxyl, pentoxyl, hexyloxyl, 2-ethylsiloxyl, heptyloxyl, octyloxyl, nonyloxyl, decyloxyl, dodecyloxyl.

By the term "$C_1$-$C_{20}$ alkylene groups" are meant linear or branched alkylene groups having 1 to 20 carbon atoms. Specific examples of $C_1$-$C_{20}$ alkylene groups are methylene, ethylene, n-propylene, iso-propylene, n-butylene, iso-butylene, t-butylene, pentylene, ethyl-hexylene, hexylene, heptylene, octylene, nonylene, decylene, dodecylene.

By the term "polyethyleneoxyl groups" are meant groups having oxyethylene units in the molecule. Specific examples of polyethyleneoxyl groups are methyloxy-ethyleneoxyl, methyloxy-diethyleneoxyl, 3-oxatetraoxyl, 3,6-dioxaheptyloxyl, 3,6,9-trioxadecyloxl, 3,6,9,12-tetraoxahexadecyloxyl.

In accordance with a preferred embodiment of the present invention, in said stage (a) said heteroaryl compound containing a terminal alkyne group having general formula (II) and said halogenated heteroaryl compound having general formula (III) may be used in molar ratios ranging from 1:2 to 1:10, preferably ranging from 1:2 to 1:5.

In accordance with a preferred embodiment of the present invention, said stage (a) may be carried out in the presence of at least one palladium-containing catalyst.

In accordance with a preferred embodiment of the present invention, in said stage (a) said palladium-containing catalyst may be selected from compounds of palladium having oxidation states of (0) or (II) such as, for example, palladium (II)chloride [$PdCl_2$], palladium(II)acetate [$Pd(OAc)_2$], tris (dibenzylidene)dipalladium(0) [$Pd_2(dba)_3$ in which dba $=C_6H_5CH=CHCOCH=CHC_6H_5$], bis(acetonitrile)palladium(II)chloride [$Pd(CH_3CN)_2Cl_2$], bis(triphenylphosphine)palladium(II)chloride [$Pd(PPh_3)_2Cl_2$], bis(triphenylphosphine)-palladium(II)acetate [$Pd(PPh_3)_2(OAc)_2$], tetrakis(triphenylphosphine)palladium(0) [$Pd(PPh_3)_4$], or mixtures thereof. Preferably, said palladium-containing catalyst may be selected from palladium (II)acetate [$Pd(OAc)_2$], bis(triphenylphosphine)palladium(II)-chloride [$Pd(PPh_3)_2C_2$], or mixtures thereof.

In accordance with a preferred embodiment of the present invention, in said stage (a) said halogenated heteroaryl compound having general formula (III) and said palladium-containing catalyst may be used in molar ratios ranging from 100:0.1 to 100:8, preferably ranging from 100:0.4 to 100:6.

In accordance with a preferred embodiment of the present invention, said stage (a) may be carried out in the presence of a catalyst containing copper in oxidation state (I) such as for example copper (I) iodide (CuI), copper (I) chloride (CuCl), copper (I) bromide (CuBr). Preferably, said catalyst containing copper in oxidation state (I) is copper (I) iodide (CuI).

In accordance with a preferred embodiment of the present invention, in stage (a) said halogenated heteroaryl compound having general formula (III) and said catalyst containing copper in oxidation state (I) may be used in molar ratios ranging from 100:0.5 to 100:20, preferably ranging from 100:1 to 100:10.

In accordance with a preferred embodiment of the present invention, said stage (a) may be carried out in the presence of at least one dipolar aprotic organic solvent.

In accordance with a preferred embodiment of the present invention, said stage (a) may be carried out in the presence of at least one dipolar aprotic organic solvent.

In accordance with a preferred embodiment of the present invention, in said stage (a) said dipolar aprotic organic solvent may be selected, for example, from triethylamine, N,N-dimethylacetamide (DMAc), dimethylsulfoxide (DMSO), N-methyl-2-pyrrolidone (NMP), N,N-dimethylformamide (DMF), or mixtures thereof. Preferably, said dipolar aprotic organic solvent may be selected from triethylamine, N,N-dimethylformamide (DMF), or mixtures thereof.

In accordance with a preferred embodiment of the present invention, in said stage (a) said halogenated heteroaryl compound having general formula (III) may be used in said dipolar aprotic organic solvent in a molar concentration ranging from 0.05 mmols/ml to 2 mmols/ml, preferably ranging from 0.1 mmols/ml to 1.5 mmols/ml.

In accordance with a preferred embodiment of the present invention, said stage (a) may be carried out at a temperature ranging from 40° C. to 130° C., preferably ranging from 50° C. to 100° C.

In accordance with a preferred embodiment of the present invention, said stage (a) may be carried out for a time ranging from 30 minutes to 12 hours, preferably ranging from 1 hour to 6 hours.

In accordance with a preferred embodiment of the present invention, the palladium-containing catalyst used in said stage (b) may be selected from palladium compounds in oxidation state (II) such as, for example, palladium(II) chloride [$PdCl_2$], palladium(II)-acetate [$Pd(OAc)_2$], palladium(II)bromide [$PdBr_2$], bis(acetonitrile)palladium(II) chloride [$Pd(CH_3CN)_2Cl_2$], bis(triphenylphosphine) palladium (II) chloride [$Pd(PPh_3)_2Cl_2$], bis(triphenylphosphine)palladium(II)acetate [$Pd(PPh_3)_2(OAc)_2$], or mixtures thereof.

Preferably, said palladium-containing catalyst is selected from palladium(II)acetate [$Pd(OAc)_2$], palladium(II)chloride [$PdCl_2$], or mixtures thereof.

In accordance with a preferred embodiment of the present invention, in said stage (b) said compound having general formula (IV) and said palladium-containing catalyst may be used in molar ratios ranging from 100:0.1 to 100:8, preferably ranging from 100:0.4 to 100:6.

In accordance with a preferred embodiment of the present invention, the copper-containing catalyst used in stage (b) may be selected from compounds of copper in oxidation state (II) such as, for example, copper(II)chloride [$CuCl_2$], copper(II)bromide [$CuBr_2$], copper(II)acetate [$Cu(OAc)_2$]. Preferably, said catalyst containing copper in oxidation state (II) is selected from copper(II)chloride [$CuCl_2$], copper(II) bromide [$CuBr_2$], or mixtures thereof.

In accordance with a preferred embodiment of the present invention, in stage (b) said compound having general formula (IV) and said catalyst containing copper in oxidation state (II) may be used in molar ratios ranging from 100:0.5 to 100:20, preferably ranging from 100:1 to 100:15.

In accordance with a preferred embodiment of the present invention, said stage (b) may be carried out in the presence of at least one dipolar aprotic organic solvent.

In accordance with a preferred embodiment of the present invention, in said stage (b) said dipolar aprotic organic solvent may be selected, for example, from N,N-dimethylacetamide (DMAc), dimethylsulfoxide (DMSO), N-methyl-2-pyrrolidone (NMP), N,N-dimethylformamide (DMF), or mixtures thereof. Preferably, said dipolar aprotic organic solvent may be selected from dimethylsulfoxide (DMSO), N,N-dimethylformamide (DMF), or mixtures thereof.

In accordance with a preferred embodiment of the present invention, in said stage (b) said compound having general formula (IV) may be used in said dipolar aprotic organic solvent in a molar concentration ranging from 0.05 mmols/l to 2 mmols/l, preferably ranging from 0.1 mmols/l to 1.5 mmols/l.

In accordance with a preferred embodiment of the present invention, said stage (b) may be carried out at a temperature ranging from 60° C. to 140° C., preferably ranging from 80° C. to 130° C.

In accordance with a preferred embodiment of the present invention, said stage (b) may be carried out for a time ranging from 30 minutes to 12 hours, preferably ranging from 1 hour to 6 hours.

In accordance with a preferred embodiment of the present invention, the iron salt used in said stage (c) may be selected, for example, from iron compounds in oxidation state (III) such as, for example, iron(III)chloride ([$FeCl_3$], iron(III) bromide [$FeBr_3$], iron(III)nitrate [$Fe(NO_3)_3$], iron(III)sulfate [$Fe_2(SO_4)_3$]. Preferably, said iron salt may be selected from iron(III)chloride [$FeCl_3$], iron(III)bromide [$FeBr_3$], or mixtures thereof.

In accordance with a preferred embodiment of the present invention, in said stage (c) said compound having general formula (V) and said iron salt may be used in molar ratios ranging from 1:1 to 1:10, preferably ranging from 1:2 to 1:5.

In accordance with a preferred embodiment of the present invention, said stage (c) may be carried out in the presence of at least one apolar organic solvent.

In accordance with a preferred embodiment of the present invention, in said stage (c) said apolar organic solvent may be selected, for example, from dichloromethane (DCM), chloroform ($CHCl_3$), chlorobenzene (CB), dichlorobenzene (DCB), or mixtures thereof. Preferably, said dipolar aprotic organic solvent may be selected from dichloromethane (DCM), chloroform ($CHCl_3$), or mixtures thereof.

In accordance with a preferred embodiment of the present invention, in said stage (c) said compound having general formula (V) may be used in said apolar organic solvent at a molar concentration ranging from 0.05 mmols/l to 2 mmols/l, preferably ranging from 0.1 mmols/l to 1.5 mmols/l.

In accordance with a preferred embodiment of the present invention, said stage (c) may be carried out at a temperature ranging from 15° C. to 60° C., preferably ranging from 20° C. to 30° C., even more preferably at ambient temperature (25° C.).

In accordance with a preferred embodiment of the present invention, said stage (c) may be carried out for a time ranging from 30 minutes to 12 hours, preferably ranging from 1 hour to 6 hours.

In accordance with a preferred embodiment of the present invention, in said stage (d) said compound having general formula (VI) and said alkyl-magnesium bromide having general formula (VII) may be used in molar ratios ranging from 1:0.5 to 1:10, preferably ranging from 1:2 to 1:7.

In accordance with a preferred embodiment of the present invention, said stage (d) may be carried out in the presence of at least one apolar organic solvent.

In accordance with a preferred embodiment of the present invention, in said stage (d) said apolar organic solvent may be selected, for example, from tetrahydrofuran (THF), diethyl ether, dioxane, or mixtures thereof. Preferably, said apolar organic solvent may be selected from tetrahydrofuran (THF), diethyl ether, or mixtures thereof.

In accordance with a preferred embodiment of the present invention, in said stage (d) said compound having general formula (VI) may be used in said apolar organic solvent at a molar concentration ranging from 0.01 mmols/l to 2 mmol/l, preferably ranging from 0.02 mmols/l to 1 mmols/l.

In accordance with a preferred embodiment of the present invention, said stage (d) may be carried out at a temperature ranging from −20° C. to 30° C., preferably ranging from −10° C. to 24° C.

In accordance with a preferred embodiment of the present invention, said stage (d) may be carried out for a time ranging from 30 minutes to 12 hours, preferably ranging from 1 hour to 6 hours.

In accordance with a preferred embodiment of the present invention, the strong organic acid used in said stage (e) may be selected, for example, from para-toluenesulfonic acid (p-TsOH), 2-naphthalenesulfonic acid, methansulfonic acid, or mixtures thereof. Preferably, said strong organic acid may be selected from para-toluenesulfonic acid (p-TsOH), 2-naphthalenesulfonic acid, or mixtures thereof.

In accordance with a preferred embodiment of the present invention, in said stage (e) said compound having general formula (VIII) and said strong organic acid may be used in molar ratios ranging from 1:0.1 to 1:1, preferably ranging from 1:0.2 to 1:0.5.

In accordance with a preferred embodiment of the present invention, said stage (e) may be carried out in the presence of at least one apolar organic solvent.

In accordance with a preferred embodiment of the present invention, in said stage (e) said apolar organic solvent may be selected, for example, from tetrahydrofuran (THF), diethyl ether, dioxane, toluene, or mixtures thereof. Preferably, said apolar organic solvent may be selected from dioxane, toluene, or mixtures thereof.

In accordance with a preferred embodiment of the present invention, in said stage (e) said compound having general formula (VIII) may be used in the same apolar organic solvent at a molar concentration ranging from 0.01 mmols/l to 2 mmols/1, preferably ranging from 0.02 mmols/l to 1.5 mmols/1.

In accordance with a preferred embodiment of the present invention, said stage (e) may be carried out at a temperature ranging from 80° C. to 170° C., preferably ranging from 100° C. to 150° C.

In accordance with a preferred embodiment of the present invention, said stage (e) may be carried out for a time ranging from 10 minutes to 3 hours, preferably ranging from 20 minutes to 2 hours.

The heteroaryl compound including a terminal alkyne group having general formula (II) and the halogenated heteroaryl compound having general formula (III), are readily commercially available.

As mentioned above, said indacen-4-one derivative may advantageously be used in the synthesis of electron-donor polymers, said polymers being a further object of the present invention.

As a consequence, the present invention also relates to a polymer comprising an indacen-4-one derivative, said polymer having general formula (IX), (X) or (XI):

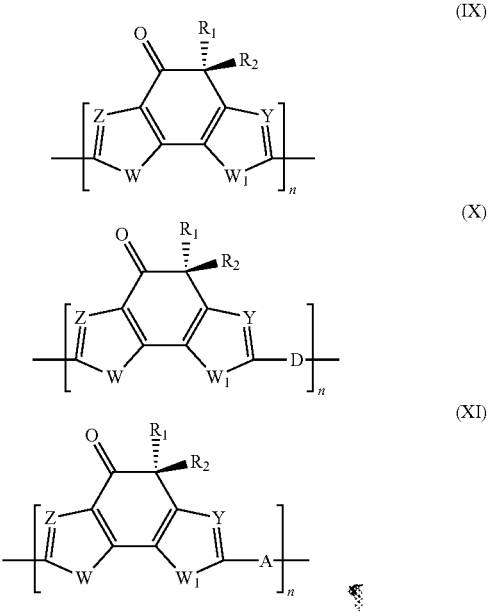

in which:
W, Z, $W_1$, $R_1$, $R_2$ and Y, have the same meanings as above reported;
D represents an electron-donor group;
A represents an electron-acceptor group;
n is an integer ranging from 10 to 500, preferably ranging from 20 to 300.

In accordance with a preferred embodiment of the present invention, said electron-donor group D may be selected, for example, from the groups reported in Table 1:

TABLE 1

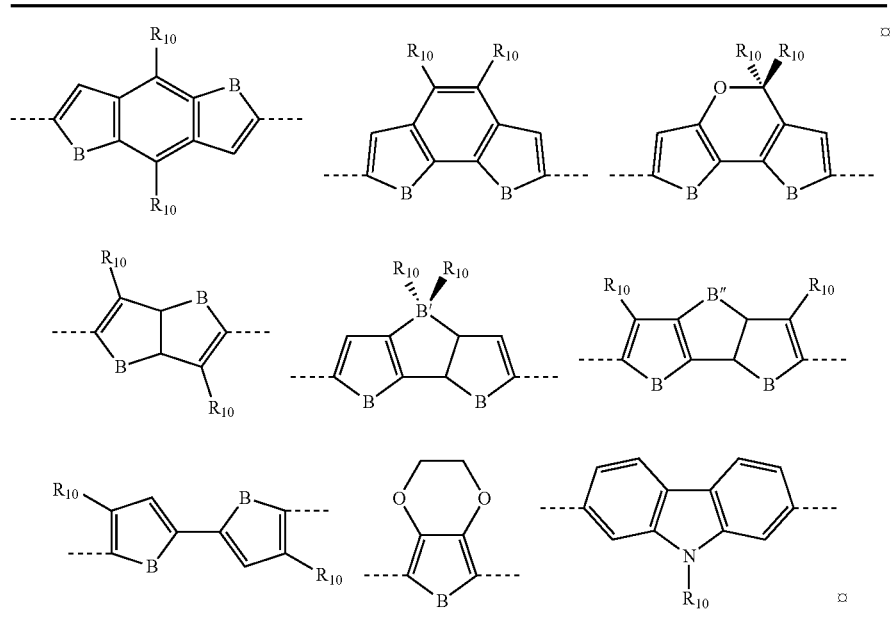

in which:

B represents a sulfur atom; an oxygen atom; a selenium atom; or an N—R group in which R represents a hydrogen atom, or is selected from linear or branched $C_1$-$C_{30}$, preferably $C_6$-$C_{26}$, alkyl groups;

B' represents a carbon atom; a silicon atom; or a germanium atom;

B" represents a sulfur atom; or an N—R group in which R has the same meanings as above reported;

$R_{10}$, which are the same or different, are selected from linear or branched $C_1$-$C_{20}$, preferably $C_2$-$C_{10}$, alkyl groups; optionally substituted cycloalkyl groups; linear or branched $C_1$-$C_{20}$, preferably $C_2$-$C_{10}$, alkoxyl groups; $R_{12}$—[—$OCH_2$—$CH_2$—]$_n$-polyethyleneoxyl groups in which $R_{12}$ is selected from linear or branched $C_1$-$C_{20}$, preferably $C_2$-$C_{10}$, alkyl groups and n is an integer ranging from 1 to 4; —$R_{13}$—$OR_{14}$ groups in which $R_{13}$ is selected from linear or branched $C_1$-$C_{20}$, preferably $C_2$-$C_{10}$, alkylene groups and $R_{14}$ represents a hydrogen atom or is selected from linear or branched $C_1$-$C_{20}$, preferably $C_2$-$C_{10}$, alkyl groups, or is selected from $R_{12}$—[—$OCH_2$—$CH_2$—]$_n$— polyethyleneoxyl groups in which $R_{12}$ has the same meanings as above reported and n is an integer ranging from 1 to 4; —$COR_{15}$ groups in which $R_{15}$ is selected from linear or branched $C_1$-$C_{20}$, preferably $C_2$-$C_{10}$, alkyl groups; —$COOR_{16}$ groups in which $R_{16}$ is selected from linear or branched $C_1$-$C_{20}$, preferably $C_2$-$C_{10}$, alkyl groups; or represent a —CHO group, or a cyano group (—CN).

In accordance with a preferred embodiment of the present invention, said electron-acceptor group A may be selected, for example, from the groups reported in Table 2:

TABLE 2

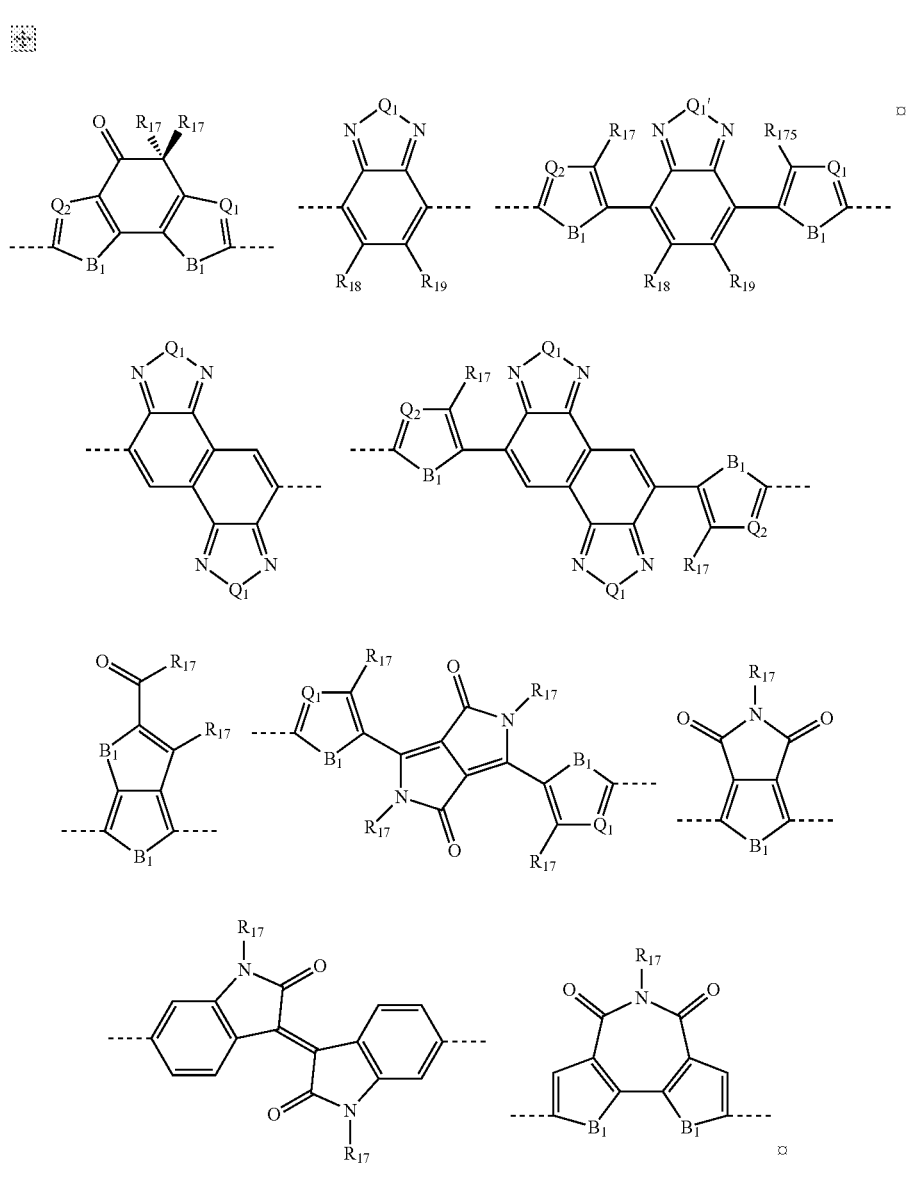

in which:

$B_1$ represents a sulfur atom; an oxygen atom; a selenium atom; an NR group in which $R_{11}$ has the same meanings as above reported;

$Q_1$ and $Q_2$, which are the same or different, represent a nitrogen atom; a sulfur atom; an oxygen atom; a selenium atom; or a C—R group in which R has the same meanings as above reported;

$R_{17}$, which are the same or different, are selected from linear or branched $C_1$-$C_{20}$, preferably $C_2$-$C_{10}$, alkyl groups; optionally substituted cycloalkyl groups; optionally substituted aryl groups; optionally substituted heteroaryl groups; linear or branched $C_1$-$C_{20}$, preferably $C_2$-$C_{10}$, alkoxyl groups; $R_{12}$—[—$OCH_2$—$CH_2$—]$_n$— polyethyleneoxyl groups in which $R_{12}$ has the same meanings as above reported and n is an integer ranging from 1 to 4; —$R_{13}$—$OR_{14}$ groups in which $R_{13}$ and $R_{14}$ have the same meanings as above reported; —$COR_{15}$ groups in which $R_{15}$ has the same meanings as above reported; —$COOR_{16}$ groups in which $R_{16}$ has the same meanings as above reported; or represent a —CHO group, or a cyano group (—CN);

$R_{18}$ and $R_{19}$, which are the same or different, represent a hydrogen atom; a fluorine atom; or are selected from linear or branched $C_1$-$C_{20}$, preferably $C_2$-$C_{10}$, alkyl groups, optionally substituted cycloalkyl groups, optionally substituted aryl groups, linear or branched $C_1$-$C_{20}$, preferably $C_2$-$C_{10}$, alkoxyl groups, $R_{12}$—[—$OCH_2$—$CH_2$—]$_n$-polyethyleneoxyl groups in which $R_{12}$ has the same meanings as above reported and n is an integer ranging from 1 to 4, —$R_{13}$—$OR_{14}$ groups in which $R_{13}$ and $R_{14}$ have the same meanings as above reported, —$COR_{15}$ groups in which $R_{15}$ has the same meanings as above reported, —$COOR_{16}$ groups in which $R_{16}$ has the same meanings as above reported, or represent a —CHO group, or a cyano group (—CN);

or, $R_{18}$ and $R_{19}$ may optionally be linked together so as to form, together with the carbon atoms to which they are linked, a cycle or a polycyclic system containing from 3 to 14 carbon atoms, preferably from 4 to 6 carbon atoms, saturated, unsaturated or aromatic, optionally containing one or more heteroatoms such a, for example, oxygen, sulfur, nitrogen, silicon, phosphorus, selenium.

The polymers comprising an indacen-4-one derivative, said polymers having general formula (IX), (X) or (XI), may be obtained by processes known in the art.

For example, in the case of a polymer having general formula (IX), said polymer may be obtained by means of a process comprising reacting at least one indacen-4-one derivative having general formula (I):

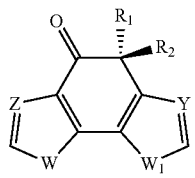

(I)

in which W, $W_1$, Z, Y, $R_1$ and $R_2$, have the same meanings as above reported, with at least one halogenated derivative of indacen-4-one having general formula (XII):

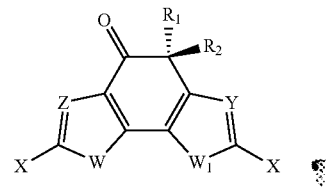

(XII)

in which W, $W_1$, Z, Y, $R_1$ and $R_2$, have the same meanings as above reported and X represents a halogen atom selected from chlorine, bromine, iodine, preferably bromine. Said process may be carried out in accordance with techniques known in the art as described, for example, by Kanbara T. et al., in the article "The effect of a solvent on direct arylation polycondensation of substituted thiophenes", "*Polymer Chemistry*" (2015), Vol. 6, pg. 891-895. Said halogenated indacen-4-one derivative having general formula (XII) may be obtained by means of processes known in the art as described, for example, by Huo L. et al., in the article "Synthesis of a polythieno[3,4-b]thiophene derivative with a low-lying HOMO level and its application in polymer solar cells", "*Chemical Communication*" (2011), Vol. 47, p. 8850-8852, above reported.

In the case of a polymer having general formula (X), said polymer may be obtained by means of a process comprising reacting at least one halogenated compound having general formula (XIII):

X-D-X  (XIII)

in which D represents an electron-donor group selected from the groups reported in Table 1 and X represents a halogen atom selected from chlorine, bromine, iodine, preferably bromine, with at least one indacen-4-one derivative having general formula (I). Said process may be carried out in accordance with techniques known in the art as described, for example, by Huo L. et al., in the article "Synthesis of a polythieno[3,4-b]thiophene derivative with a low-lying HOMO level and its application in polymer solar cells", "*Chemical Communication*" (2011), Vol. 47, pg. 8850-8852, above reported.

In the case of a polymer having general formula (XI), said polymer may be obtained by means of a process comprising reacting at least one compound having general formula (XIV):

H-A-H  (XIV)

in which A represents an electron-acceptor group selected from the groups reported in Table 2, with at least one halogenated indacen-4-one derivative having general formula (XII) above reported, or at least one compound having general formula (XV):

X-A-X  (XV)

in which A represents an electron-acceptor group selected from the groups reported in Table 2 and X represents a halogen atom selected from chlorine, bromine, iodine, preferably bromine, with at least one indacen-4-one derivative having general formula (I). Said process may be carried out in accordance with techniques known in the art as described, for example, by Ozawa F. et al., in the article "A Highly Efficient Catalyst for the Synthesis of Alternating Copolymers with Thieno[3,4-c]pyrrole-4,6-dione Units via Direct Arylation Polymerization", "*Macromolecules*" (2014), Vol. 47, pg. 626-631. Said halogenated indacen-4-one derivative having general formula (XII) may be obtained according to processes known in the art as above reported.

As above reported, said polymer having general formula (IX), (X) or (XI), may advantageously be used in the construction of photovoltaic devices (or solar devices) such as, for example, photovoltaic cells (or solar cells), photovoltaic modules (or solar modules), on either a rigid or flexible support.

A further object of the present invention is therefore a photovoltaic device (or solar device) such as, for example, a photovoltaic cell (or solar cell), a photovoltaic module (or solar module), on either a rigid or flexible support, comprising at least one polymer having general formula (IX), (X) or (XI).

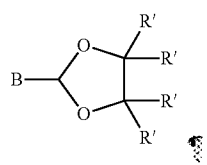

Figure 1:
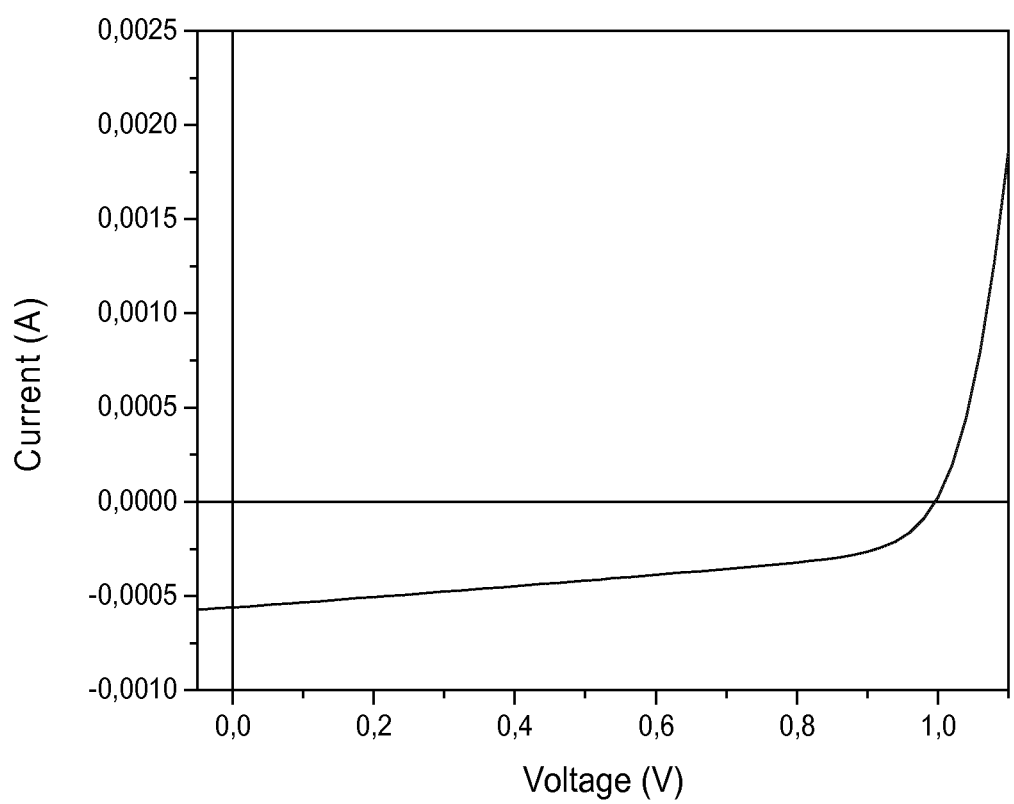
FIG. 1 shows a current-voltage curve (I-V) (Example 20)

in which the R' substituents, which are the same or different, represent a hydrogen atom, or a linear or branched $C_1$-$C_{20}$ alkyl group, and B is boron.

Some illustrative and non-limiting examples of the present invention are described below in order that it may be better understood and put into practice.

EXAMPLES

Characterisation of the Polymers Obtained
Determination of Molecular Weight

The molecular weight of the polymers obtained by working in accordance with the examples reported below was determined using Gel Permeation Chromatography (GPC) on the WATERS 150C instrument, using HT5432 columns, with trichlorobenzene eluent, at 80° C.

The weight average molecular weight ($M_w$), the number average molecular weight ($M_n$) and the polydispersion index (PDI) corresponding to the ratio $M_w/M_n$, are reported.

Example 1

Preparation of 3,3'-ethynyldithiophene Having Formula (IVa)

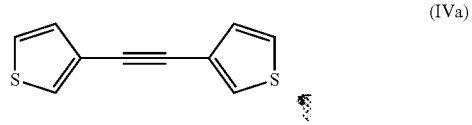 [SMILES: C(#Cc1ccsc1)c1ccsc1]

The following were placed in order in a 100 ml flask provided with a magnetic stirrer, a thermometer and cooling jacket, under an inert atmosphere: 2.163 g (20.0 mmols) of 3-ethynylthiofene (Aldrich), 40 ml of triethylamine (Aldrich), 3.912 g (24.0 mmols) of 3-bromothiophene (Aldrich), 0.076 g (0.40 mmols) of copper (1) iodide (CuI) (Aldrich), 0.140 g (0.20 mmols) of bis(triphenylphosphine)palladium(II)chloride [$PdCl_2(PPh)_3$](Aldrich): the reaction mixture obtained was heated to 80° C. and maintained, at said temperature, under stirring, for 3 hours. Subsequently, after cooling to ambient temperature (25° C.), the reaction mixture was placed in a 500 ml separating funnel: a solution of 0.1 M hydrochloric acid (HCl) (Aldrich) (3×100 ml) was added to said reaction mixture and the whole was extracted with ethyl acetate (Aldrich) (3×100 ml), yielding an acid aqueous phase and an organic phase. The entire acid aqueous phase (obtained by combining the acid aqueous phases deriving from the three extractions) was again extracted with ethyl acetate (Aldrich) (3×50 ml), yielding a further acid aqueous phase and a further organic phase. The entire organic phase (obtained by combining the organic phases deriving from the preceding three extractions and the further organic phases deriving from the further three extractions) was subsequently dried on sodium sulfate (Aldrich) and evaporated. The residue obtained was purified by elution on a silica gel chromatography column [(eluent: 9/1 n-heptane/ethyl acetate) (Carlo Erba)], yielding 3.045 g of 3,3'-ethynyldithiophene having formula (IVa) as a white solid (yield 80%).

Example 2

Preparation of 1,2-di-thiophen-3-yl-ethan-1,2-dione Having Formula (Va)

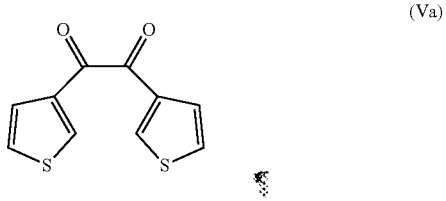 [SMILES: O=C(C(=O)c1ccsc1)c1ccsc1]

The following were added in order to a 100 ml flask provided with a magnetic stirrer, thermometer and cooling jacket under an inert atmosphere: 3,3'-ethynylthiophene obtained as described in Example 1 (3.020 g; 15.9 mmols), 120 ml of dimethyl sulfoxide (Aldrich), palladium(II)acetate [$Pd(OAc)_2$] (Aldrich) (0.357 g; 1.59 mmols), copper(II)-bromide [$Cu(Br)_2$] (Aldrich) (0.355 g; 1.59 mmols): the reaction mixture obtained was heated to 120° C. and maintained, at said temperature, under stirring, for 3 hours. Subsequently, after cooling to ambient temperature (25° C.), the reaction mixture was placed in a 500 ml separating funnel: a saturated aqueous solution of sodium chloride (Aldrich) (3×100 ml) was added to said reaction mixture and the whole was extracted with ethyl acetate (Aldrich) (3×100 ml), yielding an acid aqueous phase and an organic phase. The entire organic phase (obtained by combining the organic phases deriving from the three extractions) was washed to neutral with water (3×50 ml) and subsequently dried on sodium sulfate (Aldrich) and evaporated. The residue obtained was purified by elution on a silica gel chromatography column [(eluent: 9/1 n-heptane/ethyl acetate) (Carlo Erba)], yielding 3.045 g of 1,2-di-thiophen-3-ethyl-ethane-1,2-dione having formula (Va) as a white solid (yield 80%).

Example 3

Preparation of benzo[1,2-b:6,5-b']dithiophen-4,5-dione Having Formula (VIa)

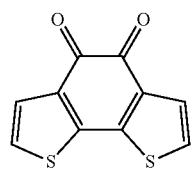
(VIa)

The following were added in order to a double-necked 250 ml Pyrex glass flask provided with a magnetic stirrer, thermometer and cooling jacket, under an inert atmosphere: 1,2-di-thiophen-3-yl-ethane-1,2-dione having formula (Va) obtained as described in Example 2 (2.890 g; 13.0 mmols), 80 ml of dichloromethane (DCM) and anhydrous iron(III) chloride [$FeCl_3$] (Aldrich) (4.922 g; 39 mmols): the reaction mixture was maintained, for 2 hours, at ambient temperature (25° C.), under stirring. Subsequently, the reaction mixture was quenched with 50 ml of distilled water and the solvent was evaporated. The residue obtained was collected and washed with distilled water (300 ml) and diethyl ether (Aldrich) (300 ml), yielding 2.606 g of benzo[1,2-b:6,5-b']dithiophen-4,5-dione having formula (VIa) as a black solid (yield 91%).

Example 4

Preparation of 4,5-dioctyl-4,5-dihydro-1,8-dithio-as-indacen-4,5-diol Having Formula (VIIIa)

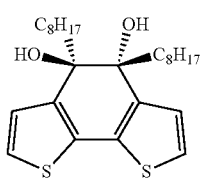
(VIIIa)

The following were added in order to a double-necked 250 ml Pyrex glass flask provided with a magnetic stirrer, thermometer and cooling jacket, under an inert atmosphere: 100 ml of anhydrous tetrahydrofuran (THF) (Aldrich), n-octyl-magnesium bromide (Aldrich) (15.655 g; 72.0 mmols), benzo[1,2-b:6,5-b']dithiophen-4,5-dione having formula (VIa) obtained as described in Example 3 (2.643 g; 12.0 mmols): the reaction mixture was cooled to 0° C. and maintained at said temperature, for 1 hour, under stirring. Subsequently, the reaction mixture was raised to ambient temperature (25° C.) and maintained at said temperature, for 3 hours, under stirring. Subsequently, the reaction mixture was placed in a 500 ml separating funnel, diluted with a saturated aqueous solution of ammonium chloride (Aldrich) (50 ml), concentrated, again diluted with a saturated aqueous solution of ammonium chloride (Aldrich) (100 ml) and extracted with ethyl acetate (Aldrich) (3×100 ml), yielding an acid aqueous phase and an organic phase. The entire organic phase (obtained by combining the organic phases deriving from the three extractions) was washed to neutral with water (3×50 ml) and subsequently dried on sodium sulfate (Aldrich) and evaporated. The residue obtained was purified by elution on a silica gel chromatography column [(eluent: 9/1 n-heptane/ethyl acetate) (Carlo Erba)], yielding 2.420 g of 4,5-dioctyl-4,5-dihydro-1,8-dithia-as-indacen-4,5-diol having formula (VIIIa) as a yellowish oil (yield 45%).

Example 5

Preparation of 5,5-dioctyl-5H-1,8-dithia-as-indacen-4-one Having Formula (Ia)

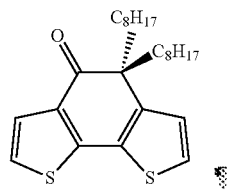
(Ia)

The following were added in order to a 100 ml flask provided with a magnetic stirrer, thermometer and cooling jacket, under an inert atmosphere: 4,5-dioctyl-4,5-dihydro-1,8-dithia-as-indacen-4,5-diol having formula (VIIIa) obtained as described in Example 4 (2.241 g; 5.00 mmols), 50 ml of toluene (Aldrich), para-toluenesulfonic acid (Aldrich) (0.162 g; 0.85 mmols): the reaction mixture was heated under reflux and maintained under reflux, for 1.5 hours, under stirring. Subsequently, after cooling to ambient temperature (25° C.), the reaction mixture was placed in a 500 ml separating funnel, diluted with a saturated aqueous solution of sodium chloride (Aldrich) (100 ml) and extracted with ethyl acetate (Aldrich) (3×50 ml) yielding an acid aqueous phase and an organic phase. The entire organic phase (obtained by combining the organic phases deriving from the three extractions) was washed to neutral with water (3×50 ml), subsequently dried on sodium sulfate (Aldrich) and evaporated. The residue obtained was purified by elution on a silica gel chromatography column [(eluent: 99/1 n-heptane/ethyl acetate) (Carlo Erba)], yielding 2.044 g of 5,5-dioctyl-5H-1,8-dithia-as-indacen-4-one having formula (Ia) as a yellowish oil (yield 95%).

Example 6

Preparation of 2,7-dibromo-5,5-dioctyl-5H-1,8-dithia-as-indacen-4-one Having Formula (XIIa)

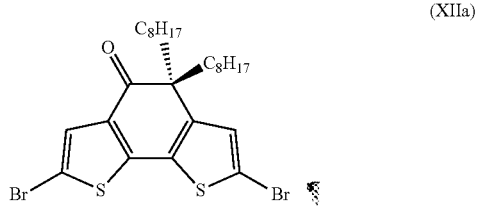

The following were added in order to a 100 ml flask provided with a magnetic stirrer, thermometer and cooling jacket, under an inert atmosphere: 5,5-dioctyl-5H-1,8-dithia-as-indacen-4-one having formula (Ia) obtained as described in Example 5 (2.0 g; 4.65 mmols), 40 ml of N,N-dimethylformamide (Aldrich), N-bromosuccinimide (Aldrich) (1.673 g; 9.40 mmols): the reaction mixture was protected from light and maintained, at ambient temperature (25° C.), for 16 hours, under stirring. Subsequently, the reaction mixture was placed in a 500 ml separating funnel: said reaction mixture was diluted with a 0.1 M solution of sodium thiosulfate (Aldrich) (100 ml) and extracted with diethyl ether (Aldrich) (3×50 ml) yielding an acid aqueous phase and an organic phase. The entire organic phase (obtained by combining the organic phases deriving from the three extractions) was washed to neutral with water (3×50 ml) and subsequently dried on sodium sulfate (Aldrich) and evaporated. The residue obtained was purified by elution on a silica gel chromatography column [(eluent: 99/1 n-heptane/ethyl acetate) (Carlo Erba)], yielding 2.517 g of 2,7-dibromo-5,5-dioctyl-5H-1,8-dithia-as-indacen-4-one having formula (XIIa) as a greenish solid (yield 92%).

Example 7

Preparation of the Polymer Having Formula (IXa)

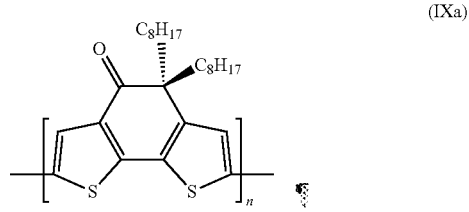

The following were added in order to a 30 ml Pyrex glass tailed test-tube provided with a screw stopper, a magnetic stirrer, thermometer and cooling jacket, under inert atmosphere: 5,5-dioctyl-5H-1,8-dithia-as-indacen-4-one having formula (Ia) obtained in Example 5 (0.216 g, 0.50 mmol), 2,7-dibromo-5,5-dioctyl-5H-1,8-dithia-as-indacen-4-one having formula (XIIa) obtained in Example 6 (0.294 g, 0.50 mmol), caesium carbonate (Aldrich) (0.489 g, 1.50 mmol), pivalic acid (0.051 g, 0.50 mmol) and tris(dibenzylideneacetone)dipalladium(0) [Pd$_2$(dba)$_3$] (Aldrich) (0.0023 g, 0.0025 mmol). Subsequently, the reactor underwent 3 vacuum-argon cycles and finally ortho-xylene (Aldrich) (1 ml) was added under a flow of argon. The reactor was then placed in an oil bath preheated to 100° C. and maintained, at said temperature, for 24 hours, under magnetic stirring. The colour of the reaction mixture became purple after 3 hours and became dark purple at the end of the reaction (i.e. after 24 hours). Subsequently, after cooling to ambient temperature (25° C.), the reaction mixture obtained was placed in methanol (100 ml) and the precipitate obtained underwent sequential extraction in a Soxhlet apparatus with methanol (Aldrich), acetone (Aldrich), n-heptane (Aldrich) and, finally, chloroform (Aldrich). The organic phase obtained (50 ml) was concentrated under reduced atmosphere and precipitated from methanol (100 ml) (Aldrich). The precipitate obtained was collected and dried under vacuum, for 16 hours, at 50° C., yielding 0.182 g of a dark red solid product (yield 85%) corresponding to the polymer having formula (IXa). The molecular weight of said solid product was determined by Gel Permeation Chromatography (GPC) working as above reported, obtaining the following data:
($M_w$)=4621 Dalton;
($M_n$)=2809 Dalton;
(PDI)=1.7868.

Example 8

Preparation of the Copolymer Having Formula (XIa)

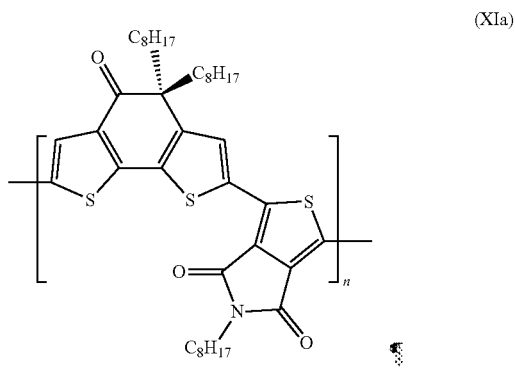

The following were added in order to a 30 ml Pyrex glass tailed test-tube provided with a screw stopper, a magnetic stirrer, thermometer and cooling jacket, under inert atmosphere: 5,5-dioctyl-5H-1,8-dithia-as-indacen-4-one having formula (Ia) obtained as described in Example 5 (0.216 g, 0.50 mmol), 1,3-dibromo-5-octyl-4H-thieno[3,4-c]pyrrole-4,6(5H)-dione (Aldrich) (0.212 g, 0.50 mmol), caesium carbonate (Aldrich) (0.489 g, 1.50 mmol), pivalic acid (Aldrich) (0.051 g, 0.50 mmol) and tris(dibenzylideneacetone)dipalladium(0) [Pd$_2$(dba)$_3$] (Aldrich) (0.0023 g, 0.0025 mmol). Subsequently, the reactor underwent 3 vacuum-argon cycles and finally ortho-xylene (Aldrich) (1 ml) was added under a flow of argon. The reactor was then placed in an oil bath preheated to 100° C. and maintained at said temperature, for 24 hours, under magnetic stirring. The colour of the reaction mixture became purple after 3 hours and became dark purple at the end of the reaction (i.e. after 24 hours). Subsequently, after cooling to ambient temperature (25° C.), the reaction mixture obtained was placed in methanol (100 ml) and the precipitate obtained underwent sequential extraction in Soxhlet apparatus with methanol (Aldrich), acetone (Aldrich), n-heptane (Aldrich) and finally chloroform (Aldrich). The organic phase obtained (50 ml) was concentrated in a reduced atmosphere and precipitated from methanol (100 ml) (Aldrich). The precipitate obtained was collected and dried under vacuum at 50° C. for 16 hours, yielding 0.277 g of a dark purple solid product (yield 80%), corresponding to the copolymer having formula (XIa). The molecular weight of said solid product was determined by Gel Permeation Chromatography (GPC) operating as above reported, yielding the following data:
- $(M_w)$=8380 Dalton;
- $(M_n)$=6111 Dalton;
- (PDI)=1.4512.

Example 9

Preparation of the Copolymer Having Formula (XIa)

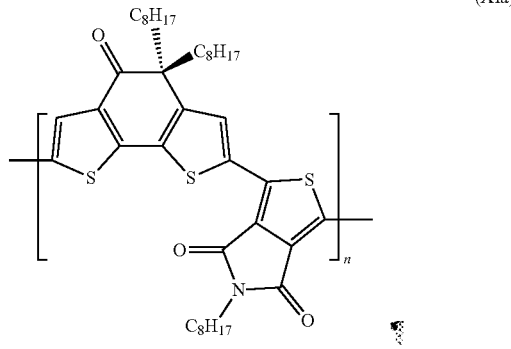

The following were added in order to a 30 ml Pyrex glass tailed test-tube provided with a screw stopper, a magnetic stirrer, thermometer and cooling jacket, under inert atmosphere: 2,7-dibromo-5,5-dioctyl-5H-1,8-dithia-as-indacen-4-one having formula (XIIa) obtained as described in Example 6 (1.766 g, 3.00 mmol), 5-octylthieno[3,4-c]pyrrole-4,6-dione (Aldrich) (0.796 g, 3.00 mmol), caesium carbonate (Aldrich) (2.933 g, 15.00 mmol), pivalic acid (Aldrich) (0.306 g, 3.00 mmol) and tris(dibenzylideneacetone)-dipalladium(0) [Pd$_2$(dba)$_3$] (Aldrich) (0.014 g, 0.015 mmol). Subsequently, the reactor underwent 3 vacuum-argon cycles and finally ortho-xylene (Aldrich) (6 ml) was added under a flow of argon. The reactor was then placed in an oil bath preheated to 100° C. and maintained at said temperature, for 24 hours, under magnetic stirring. The colour of the reaction mixture became purple after 3 hours and became dark purple at the end of the reaction (i.e. after 24 hours). Subsequently, after cooling to ambient temperature (25° C.), the reaction mixture obtained was placed in methanol (300 ml) and the precipitate obtained underwent sequential extraction in Soxhlet apparatus with methanol (Aldrich), acetone (Aldrich), n-heptane (Aldrich) and finally chloroform (Aldrich). 50 ml of a 30% concentrated aqueous ammonia solution (Aldrich) was added to the organic phase obtained (50 ml) and the whole was placed, under stirring, at 60° C., for 30 minutes. Subsequently, the whole was allowed to cool to ambient temperature (25° C.) and extracted with distilled water (3×50 ml). 50 ml of a 30% concentrated aqueous ammonia solution (Aldrich) were added to the entire organic phase (obtained by combining the organic phases deriving from the three extractions) (50 ml) and the whole was placed, under stirring, at 60° C., for 30 minutes. Subsequently, the whole was allowed to cool to ambient temperature (25° C.) and extracted with distilled water (3×50 ml). The entire organic phase (obtained by combining the organic phases deriving from the three extractions) (50 ml) was concentrated in a reduced atmosphere and precipitated from methanol (300 ml) (Aldrich). The precipitate obtained was collected and dried under vacuum, for 16 hours, at 50° C., yielding 1.557 g of a dark purple solid product (yield 75%) corresponding to the copolymer having formula (XIa).

The molecular weight of said solid product was determined by Gel Permeation Chromatography (GPC) working as above reported, and the following data were obtained:
- $(M_w)$=203585 Dalton;
- $(M_n)$=56340 Dalton;
- (PDI)=3.6135.

Example 10

Preparation of the Copolymer Having Formula (Xa)

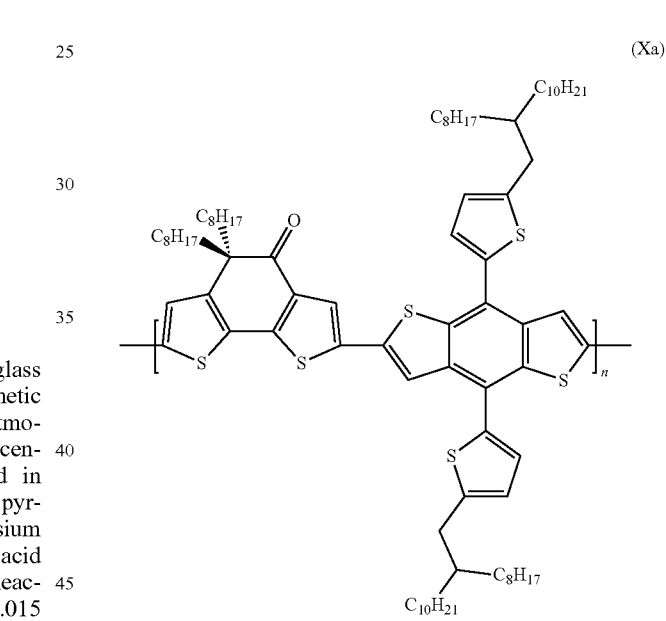

The following were added in order to a 30 ml Pyrex glass tailed test-tube provided with a screw stopper, a magnetic stirrer, thermometer and cooling jacket, under inert atmosphere:2,7-dibromo-5,5-dioctyl-5H-1,8-dithia-as-indacen-4-one having formula (XIIa) obtained as described in Example 6 (1.766 g, 3.00 mmol), 4,8-bis(2-(5-(2-octyldodecyl))thienyl)benzo[1,2-b:4,5-b']dithiophene (SunaTech) (3.083 g, 3.00 mmol), caesium carbonate (Aldrich) (2.933 g, 15.00 mmol), pivalic acid (Aldrich) (0.306 g, 3.00 mmol) and tris(dibenzylideneacetone)dipalladium(0) [Pd$_2$(dba)$_3$] (Aldrich) (0.014 g, 0.015 mmol). Subsequently, the reactor underwent 3 vacuum-argon cycles and finally ortho-xylene (Aldrich) (6 ml) was added under a flow of argon. The reactor was then placed in an oil bath preheated to 100° C. and maintained at said temperature, for 24 hours, under magnetic stirring. The colour of the reaction mixture became red after 3 hours and became dark red at the end of the reaction (i.e. after 24 hours). Subsequently, after cooling to ambient temperature (25° C.), the reaction mixture obtained was placed in methanol (300 ml) and the precipitate obtained underwent sequential extraction in Soxhlet apparatus with methanol (Aldrich), acetone (Aldrich), n-heptane (Aldrich) and finally chloroform (Aldrich). 50 ml of a 30% concentrated aqueous ammonia solution (Aldrich) was added to the organic phase obtained (50 ml) and the whole was placed, under stirring, at 60° C., for 30 minutes. Subsequently, the whole was allowed to cool to ambient temperature (25° C.) and extracted with distilled water (3×50 ml). 50 ml of a 30% concentrated aqueous ammonia solution (Aldrich) were added to the entire organic phase (obtained by combining the organic phases deriving from the three extractions) (50 ml) and the whole was placed, under stirring, at 60° C., for 30 minutes. Subsequently, the whole was allowed to cool to ambient temperature (25° C.) and extracted with distilled water (3×50 ml). The entire organic phase (obtained by combining the organic phases deriving from the three extractions) (50 ml) was concentrated in a reduced atmosphere and precipitated from methanol (300 ml) (Aldrich). The precipitate obtained was collected and dried under vacuum, for 16 hours, at 50° C., yielding 2.610 g of a dark red solid product (yield 65%) corresponding to the copolymer having formula (Xa).

The molecular weight of said solid product was determined by Gel Permeation Chromatography (GPC) working as above reported, and the following data were obtained:
($M_w$)=36860 Dalton;
($M_n$)=17957 Dalton;
(PDI)=2.0527.

Example 11

Preparation of 4,5-bis(3,7-dimethyloctyl)-4,5-dihydro-1,8-dithio-as-indacen-4,5-diol Having Formula (VIIIb)

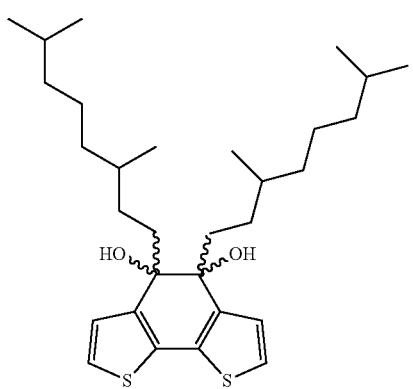

(VIIIb)

The following were added in order to a double-necked 250 ml Pyrex glass flask provided with a magnetic stirrer, thermometer and cooling jacket, under an inert atmosphere: 100 ml of anhydrous tetrahydrofuran (THF) (Aldrich), 3,7-dimethyl-octyl-magnesium bromide (Aldrich) (17.675 g; 72.0 mmols), benzo[1,2-b:6,5-b']dithiophen-4,5-dione having formula (VIa) obtained as described in Example 3 (2.643 g; 12.0 mmols): the reaction mixture was cooled to 0° C. and maintained at said temperature, for 1 hour, under stirring. Subsequently, the reaction mixture was raised to ambient temperature (25° C.) and maintained at said temperature, for 3 hours, under stirring. Subsequently, the reaction mixture was placed in a 500 ml separating funnel, diluted with a saturated aqueous solution of ammonium chloride (Aldrich) (50 ml), concentrated, again diluted with a saturated aqueous solution of ammonium chloride (Aldrich) (100 ml) and extracted with ethyl acetate (Aldrich) (3×100 ml), yielding an acid aqueous phase and an organic phase. The entire organic phase (obtained by combining the organic phases deriving from the three extractions) was washed to neutral with water (3×50 ml) and subsequently dried on sodium sulfate (Aldrich) and evaporated. The residue obtained was purified by elution on a silica gel chromatography column [(eluent: 9/1 n-heptane/ethyl acetate) (Carlo Erba)], yielding 2.908 g of 4,5-bis(3,7-dimethyloctyl)-4,5-dihydro-1,8-dithia-as-indacen-4,5-diol having formula (VIIIb) as a yellowish oil (yield 48%).

Example 12

Preparation of 5,5-bis(3,7-dimethyloctyl)-5H-1,8-dithia-as-indacen-4-one Having Formula (Ib)

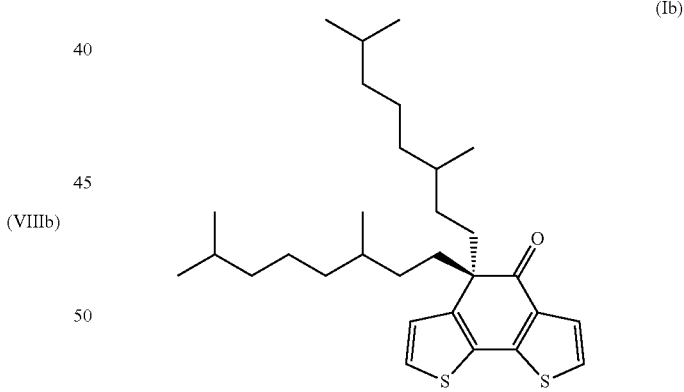

(Ib)

The following were added in order to a 100 ml flask provided with a magnetic stirrer, thermometer and cooling jacket, under an inert atmosphere: 4,5-bis(3,7-dimethyloctyl)-4,5-dihydro-1,8-dithia-as-indacen-4,5-diol having formula (VIIIb) obtained as described in Example 11 (2.524 g; 5.00 mmols), 50 ml of toluene (Aldrich), para-toluenesulfonic acid (Aldrich) (0.162 g; 0.85 mmols): the reaction mixture was heated under reflux and maintained under reflux, for 1.5 hours, under stirring. Subsequently, after cooling to ambient temperature (25° C.), the reaction mixture was placed in a 500 ml separating funnel, diluted with a saturated aqueous solution of sodium chloride (Aldrich)

(100 ml) and extracted with ethyl acetate (Aldrich) (3×50 ml) yielding an acid aqueous phase and an organic phase. The entire organic phase (obtained by combining the organic phases deriving from the three extractions) was washed to neutral with water (3×50 ml), subsequently dried on sodium sulfate (Aldrich) and evaporated. The residue obtained was purified by elution on a silica gel chromatography column [(eluent: 99/1 n-heptane/ethyl acetate) (Carlo Erba)], yielding 2.312 g of 5,5-bis(3,7-dimethyloctyl)-5H-1,8-dithia-as-indacen-4-one having formula (Ib) as a yellowish oil (yield 95%).

Example 13

Preparation of 2,7-dibromo-5,5-dioctyl-5H-1,8-dithia-as-indacen-4-one Having Formula (XIIb)

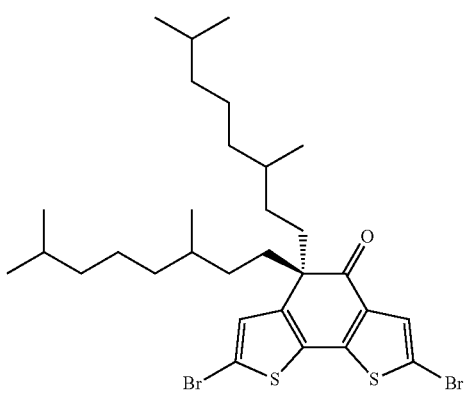

(XIIb)

The following were added in order to a 100 ml flask provided with a magnetic stirrer, thermometer and cooling jacket, under an inert atmosphere: 5,5-bis(3,7-dimethyloctyl)-5H-1,8-dithia-as-indacen-4-one having formula (Ib) obtained as described in Example 12 (2.434 g; 5.00 mmols), 40 ml of N,N-dimethylformamide (Aldrich), N-bromosuccinimide (Aldrich) (1.797 g; 10.01 mmols): the reaction mixture was protected from light and maintained, at ambient temperature (25° C.), for 16 hours, under stirring. Subsequently, the reaction mixture was placed in a 500 ml separating funnel: said reaction mixture was diluted with a 0.1 M solution of sodium thiosulfate (Aldrich) (100 ml) and extracted with diethyl ether (Aldrich) (3×50 ml) yielding an acid aqueous phase and an organic phase. The entire organic phase (obtained by combining the organic phases deriving from the three extractions) was washed to neutral with water (3×50 ml) and subsequently dried on sodium sulfate (Aldrich) and evaporated. The residue obtained was purified by elution on a silica gel chromatography column [(eluent: 99/1 n-heptane/ethyl acetate) (Carlo Erba)], yielding 2.965 g of 2,7-dibromo-5,5-bis(3,7-dimethyloctyl)-5H-1,8-dithia-as-indacen-4-one having formula (XIIb) as a greenish solid (yield 92%).

Example 14

Preparation of the Copolymer Having Formula (XIa)

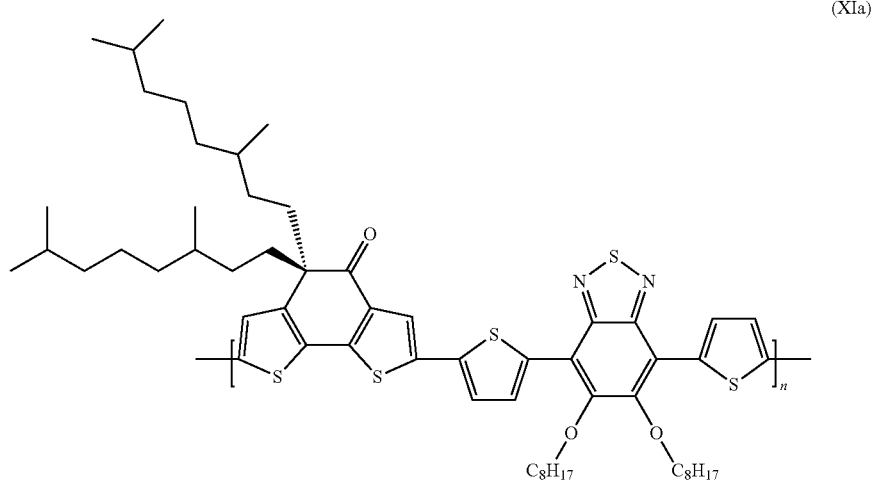

(XIa)

The following were added in order to a 30 ml Pyrex glass tailed test-tube provided with a screw stopper, a magnetic stirrer, thermometer and cooling jacket, under inert atmosphere: 2,7-dibromo-5,5-bis(3,7-dimethyloctyl)-5H-1,8-dithia-as-indacen-4-one having formula (XIIb) obtained as described in Example 13 (1.934 g, 3.00 mmol), 5,6-bis(octyloxy)-4,7-bis(thiophen-2-yl)-2,1,3-benzothiadiazole (CaLos) (1.670 g, 3.00 mmol), caesium carbonate (Aldrich) (2.933 g, 15.00 mmol), pivalic acid (Aldrich) (0.306 g, 3.00 mmol) and tris(dibenzylideneacetone)dipalladium(0) [$Pd_2(dba)_3$] (Aldrich) (0.014 g, 0.015 mmol). Subsequently, the reactor underwent 3 vacuum-argon cycles and finally orthoxylene (Aldrich) (6 ml) was added under a flow of argon. The reactor was then placed in an oil bath preheated to 100° C. and maintained at said temperature, for 24 hours, under magnetic stirring. The colour of the reaction mixture became red after 3 hours and became dark red at the end of the reaction (i.e. after 24 hours). Subsequently, after cooling to ambient temperature (25° C.), the reaction mixture obtained was placed in methanol (300 ml) and the precipitate obtained underwent sequential extraction in Soxhlet apparatus with methanol (Aldrich), acetone (Aldrich), n-heptane (Aldrich) and finally chloroform (Aldrich). 50 ml of a 30% concentrated aqueous ammonia solution (Aldrich) was added to the organic phase obtained (50 ml) and the whole was placed, under stirring, at 60° C., for 30 minutes. Subsequently, the whole was allowed to cool to ambient temperature (25° C.) and extracted with distilled water (3×50 ml). 50 ml of a 30% concentrated aqueous ammonia solution (Aldrich) were added to the entire organic phase (obtained by combining the organic phases deriving from the three extractions) (50 ml) and the whole was placed, under stirring, at 60° C., for 30 minutes. Subsequently, the whole was allowed to cool to ambient temperature (25° C.) and extracted with distilled water (3×50 ml). The entire organic phase (obtained by combining the organic phases deriving from the three extractions) (50 ml) was concentrated in a reduced atmosphere and precipitated from methanol (300 ml) (Aldrich). The precipitate obtained was collected and dried under vacuum, for 16 hours, at 50° C., yielding 2.027 g of a dark red solid product (yield 65%) corresponding to the copolymer having formula (Xa).

The molecular weight of said solid product was determined by Gel Permeation Chromatography (GPC) working as above reported, and the following data were obtained:

($M_w$)=21075 Dalton;
($M_n$)=128779 Dalton;
(PDI)=1.6364.

Example 15

Preparation of 4,5-didecyl-4,5-dihydro-1,8-dithio-as-indacen-4,5-diol Having Formula (VIIIc)

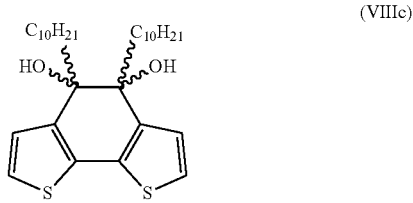

(VIIIc)

The following were added in order to a double-necked 250 ml Pyrex glass flask provided with a magnetic stirrer, thermometer and cooling jacket, under an inert atmosphere: 100 ml of anhydrous tetrahydrofuran (THF) (Aldrich), n-decyl-magnesium bromide (Aldrich) (17.675 g; 72.0 mmols), benzo[1,2-b:6,5-b']dithiophen-4,5-dione having formula (VIa) obtained as described in Example 3 (2.643 g; 12.0 mmols): the reaction mixture was cooled to 0° C. and maintained at said temperature, for 1 hour, under stirring. Subsequently, the reaction mixture was raised to ambient temperature (25° C.) and maintained at said temperature, for 3 hours, under stirring. Subsequently, the reaction mixture was placed in a 500 ml separating funnel, diluted with a saturated aqueous solution of ammonium chloride (Aldrich) (50 ml), concentrated, again diluted with a saturated aqueous solution of ammonium chloride (Aldrich) (100 ml) and extracted with ethyl acetate (Aldrich) (3×100 ml), yielding an acid aqueous phase and an organic phase. The entire organic phase (obtained by combining the organic phases deriving from the three extractions) was washed to neutral with water (3×50 ml) and subsequently dried on sodium sulfate (Aldrich) and evaporated. The residue obtained was purified by elution on a silica gel chromatography column [(eluent: 9/1 n-heptane/ethyl acetate) (Carlo Erba)], yielding 2.385 g of 4,5-didecyl-4,5-dihydro-1,8-dithia-as-indacen-4,5-diol having formula (VIIIc) as a yellowish oil (yield 45%).

Example 16

Preparation of 5,5-didecyl-5H-1,8-dithia-as-indacen-4-one Having Formula (Ic)

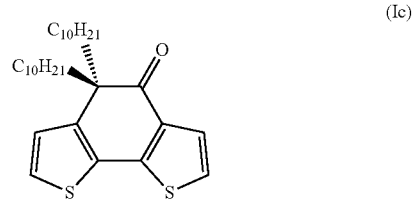

(Ic)

The following were added in order to a 100 ml flask provided with a magnetic stirrer, thermometer and cooling jacket, under an inert atmosphere: 4,5-didecyl-4,5-dihydro-1,8-dithia-as-indacen-4,5-diol having formula (VIIIc) obtained as described in Example 15 (2.524 g; 5.00 mmols), 50 ml of toluene (Aldrich), para-toluenesulfonic acid (Aldrich) (0.162 g; 0.85 mmols): the reaction mixture was heated under reflux and maintained under reflux, for 1.5 hours, under stirring. Subsequently, after cooling to ambient temperature (25° C.), the reaction mixture was placed in a 500 ml separating funnel, diluted with a saturated aqueous solution of sodium chloride (Aldrich) (100 ml) and extracted with ethyl acetate (Aldrich) (3×50 ml) yielding an acid aqueous phase and an organic phase. The entire organic phase (obtained by combining the organic phases deriving from the three extractions) was washed to neutral with water (3×50 ml), subsequently dried on sodium sulfate (Aldrich) and evaporated. The residue obtained was purified by elution on a silica gel chromatography column [(eluent: 99/1 n-heptane/ethyl acetate) (Carlo Erba)], yielding 2.385 g of 5,5-didecyl-5H-1.8-dithia-as-indacen-4-one having formula (Ic) as a yellowish oil (yield 98%).

Example 17

Preparation of 2,7-dibromo-5,5-didecyl-5H-1,8-dithia-as-indacen-4-one Having Formula (XIIc)

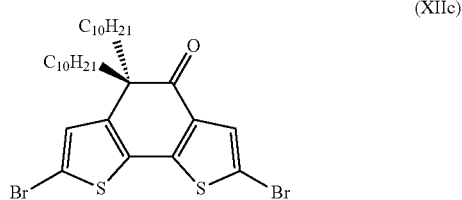

(XIIc)

The following were added in order to a 100 ml flask provided with a magnetic stirrer, thermometer and cooling jacket, under an inert atmosphere: 5,5-didecyl-5H-1,8-dithia-as-indacen-4-one having formula (Ic) obtained as described in Example 16 (2.434 g; 5.00 mmols), 40 ml of N,N-dimethylformamide (Aldrich), N-bromosuccinimide (Aldrich) (1.797 g; 10.01 mmols): the reaction mixture was protected from light and maintained, at ambient temperature (25° C.), for 16 hours, under stirring. Subsequently, the reaction mixture was placed in a 500 ml separating funnel: said reaction mixture was diluted with a 0.1 M solution of sodium thiosulfate (Aldrich) (100 ml) and extracted with diethyl ether (Aldrich) (3×50 ml) yielding an acid aqueous phase and an organic phase. The entire organic phase (obtained by combining the organic phases deriving from the three extractions) was washed to neutral with water (3×50 ml) and subsequently dried on sodium sulfate (Aldrich) and evaporated. The residue obtained was purified by elution on a silica gel chromatography column [(eluent: 99/1 n-heptane/ethyl acetate) (Carlo Erba)], yielding 3.062 g of 2,7-dibromo-5,5-didecyl-5H-1,8-dithia-as-indacen-4-one having formula (XIIc) as a yellow-green solid (yield 95%).

Example 18

Preparation of the Copolymer Having Formula (Xb)

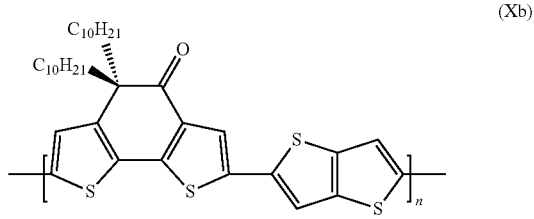

(Xb)

The following were added in order to a 30 ml Pyrex glass tailed test-tube provided with a screw stopper, a magnetic stirrer, thermometer and cooling jacket, under inert atmosphere: 2,7-dibromo-5,5-didecyl-5H-1,8-dithia-as-indacen-4-one having formula (XIIc) obtained as described in Example 17 (1.934 g, 3.00 mmol), thieno[3,2-b]thiophene (Aldrich) (0,421 g, 3.00 mmol), caesium carbonate (Aldrich) (2.933 g, 15.00 mmol), pivalic acid (Aldrich) (0.306 g, 3.00 mmol) and tris(dibenzylidene-acetone)dipalladium(0) [$Pd_2(dba)_3$] (Aldrich) (0.014 g, 0.015 mmol). Subsequently, the reactor underwent 3 vacuum-argon cycles and finally ortho-xylene (Aldrich) (6 ml) was added under a flow of argon. The reactor was then placed in an oil bath preheated to 100° C. and maintained at said temperature, for 24 hours, under magnetic stirring. The colour of the reaction mixture became red after 3 hours and became dark red at the end of the reaction (i.e. after 24 hours). Subsequently, after cooling to ambient temperature (25° C.), the reaction mixture obtained was placed in methanol (300 ml) and the precipitate obtained underwent sequential extraction in Soxhlet apparatus with methanol (Aldrich), acetone (Aldrich), n-heptane (Aldrich) and finally chloroform (Aldrich). 50 ml of a 30% concentrated aqueous ammonia solution (Aldrich) was added to the organic phase obtained (50 ml) and the whole was placed, under stirring, at 60° C., for 30 minutes. Subsequently, the whole was allowed to cool to ambient temperature (25° C.) and extracted with distilled water (3×50 ml). 50 ml of a 30% concentrated aqueous ammonia solution (Aldrich) were added to the entire organic phase (obtained by combining the organic phases deriving from the three extractions) (50 ml) and the whole was placed, under stirring, at 60° C., for 30 minutes. Subsequently, the whole was allowed to cool to ambient temperature (25° C.) and extracted with distilled water (3×50 ml). The entire organic phase (obtained by combining the organic phases deriving from the three extractions) (50 ml) was concentrated in a reduced atmosphere and precipitated from methanol (300 ml) (Aldrich). The precipitate obtained was collected and dried under vacuum, for 16 hours, at 50° C., yielding 1.495 g of a dark red solid product (yield 80%) corresponding to the copolymer having formula (Xb). The molecular weight of said solid product was determined by Gel Permeation Chromatography (GPC) working as above reported, and the following data were obtained:

$(M_w)$=46674 Dalton;
$(M_n)$=24961 Dalton;
(PDI)=1.8903.

Example 19

Reference Cell

Figure 4:
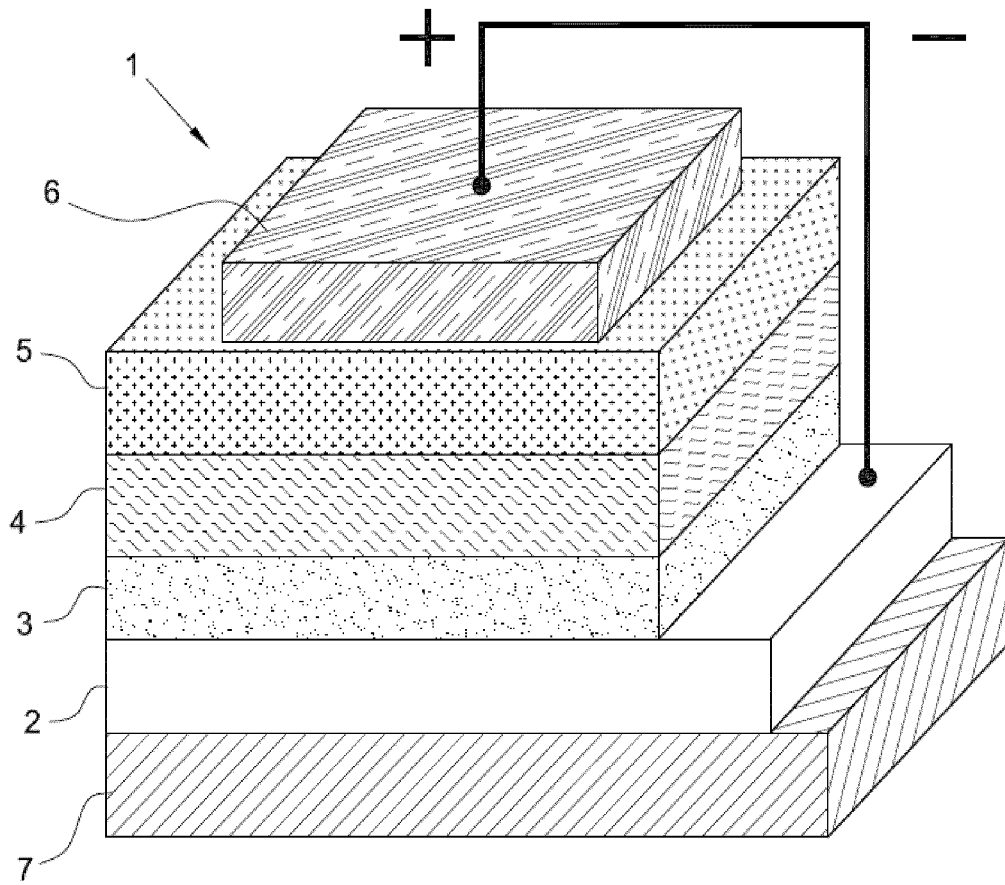
FIG. 4 shows a schematic representation of an inverted polymer solar cell (Examples 19-21)

FIG. 4 is a schematic representation of an inverted polymer solar cell used in Examples 19-21.

To this aim, a polymer based device was prepared on a ITO (Indium Tin Oxide) coated glass substrate (Kintec Company—Hong Kong), previously submitted to a cleaning procedure consisting in a manual cleaning, wiping with a lint-free cloth soaked with a detergent diluted in tap water. The substrates were then rinsed with tap water. Successively, the substrates were thoroughly cleaned according to the following methods in sequence: ultrasonic baths in (i) distilled water plus detergent (followed by manual drying with a lint-free cloth); (ii) distilled water (followed by manual drying with a lint-free cloth); (iii) acetone and (iv) isopropanol in sequence. In particular, the substrates were arranged in a becker containing the solvent, located in a ultrasonic bath, kept at ambient temperature, for a 10 minutes treatment. After treatments (iii) and (iv), each substrate was dried with a compressed nitrogen flux. Subsequently, the glass/ITO was further cleaned in an air plasma cleaner (Tucano type—Gambetti), immediately before proceeding to the next stage. The so treated substrate was ready for the deposition of the first layer. The ZnO layer was obtained via a sol-gel process starting from the precursor solution prepared as disclosed in Example 1 of International Patent Application WO 2015/068102 in the name of the Applicant which is hereby incorporated by reference. The solution was spin-casted on the substrate rotating at 600 rpm for 150 sec, followed by rotating at 1500 rpm for 5 sec. Immediately after the layer deposition, the ZnO formation was obtained by thermically treating the device, at 140° C., for 5 min, on a hot plate, in ambient air. The so obtained layer had a thickness of 30 nm and it was partially removed with iso-propanol 0.1 M, leaving the layer only on the desired area. In order to obtain a correct deposition, the ambient temperature has to be ranging from 18° C. to 21° C. and the relative humidity of the ambient has to be ranging from 3% to 45%.

The active layer, composed by poly-3-hexylthiophene and [6,6]-phenyl-$C_{71}$-butyric acid methyl ester (P3HT:PC[71] BM), was spin-casted from a solution 1:0.8 (w/w) in chlorobenzene with a P3HT concentration of 10 mg/ml, which was kept under stirring, at 50° C., overnight. The thin film was obtained by rotation at 300 rpm (acceleration 255 rpm/sec) for 90 sec. The thickness of the layer resulted to be 250 nm (measured on a test cell).

Above the so obtained layer, a third layer was deposited, namely the anodic buffer layer, which was obtained by depositing a commercial molybdenum oxide ($MoO_3$) through thermic process: the thickness of the layer 10 nm. On top of the layer stack, a 100 nm thick silver (Ag) anode was evaporated, suitably masking the device area so as to obtain an active area of 25 $mm^2$. The depositions of the two last layers were carried out in a standard thermal evaporation chamber containing the substrate and two resistance-heated evaporation vessels containing 10 mg of a molybdenum oxide ($MoO_3$) in powder form and 10 silver (Ag) shots (diameter 1-3 mm), respectively. The evaporation process was carried out under vacuum at a pressure of about $1\times10^{-6}$ bar. The evaporated molybdenum oxide ($MoO_3$) and silver (Ag) condensed on the unmasked regions of the substrate. The thickness of the layers was measured with a profilometer Dektak 150 (Veeco Instruments Inc.).

The electrical characterization of the device was performed, in ambient atmosphere, just the device construction was terminated.

The current-voltage curves (I-V) were recorded with a multimeter Keithley© 2600A connected to a personal computer for data collection. Photocurrent was measured by exposing the device to the light of a ABET SUN© 2000-4 sun simulator, able to provide an AM 1.5G irradiation with an intensity of 100 mW/$cm^2$ (1 sun), measured with a Ophir Nova© II powermeter connected to a thermal sensor 3A-P. The device, in particular, was masked, so as to obtain an effective area equal to 0.16 $mm^2$. In Table 3 the four characteristic parameters are reported as average values.

The external quantum efficiency (EQE) curves were registered under a monochromatic light (obtained by a monochromator TMc300F-U (I/C)-Triple grating monochromator and a double source with a Xenon lamp and a halogen with quartz lamp) into a customized tool of Bentham Instrument Ltd. All the preparation stages, as well as the all the characterization measurements of the device, were not expressly mentioned, were carried out in air.

Example 20

Cell Containing Copolymer Having Formula (Xb)

The substrate was cleaned as described for the reference sample (Example 19) and subsequently treated with air plasma.

The substrate was then ready for the deposition of the first layer, i.e. the ZnO layer, as described in Example 19, having a thickness of 30 nm. Subsequently, the active layer composed by copolymer having formula (Xb) obtained as described in Example 18 and [6,6]-phenyl-$C_{71}$-butyric acid methyl ester (P3HT:PC[71]BM), was spin-casted from a solution 1:2 (w/w) in chlorobenzene+2% chloronaphthalene with a copolymer having formula (Xb) concentration of 24 mg/ml. The thin film was obtained by rotation at 5000 rpm (acceleration 2500 rpm/sec) for 90 sec. The thickness of the layer resulted to be 60 nm (measured on a test cell). The remaining layers was deposited as described in Example 19.

The electrical characterization of the device was performed, in ambient atmosphere, just the device construction was terminated, operating as described in Example 19: the obtained results are given in Table 3. In FIG. 1 was reported the current-voltage curve (I-V) obtained [in abscissa was reported the voltage in volts (V); in the ordinate was reported the current in ampere (A)].

Example 21

Cell Containing Copolymer Having Formula (XIa)

The substrate was cleaned as described for the reference sample (Example 19) and subsequently treated with air plasma.

The substrate was then ready for the deposition of the first layer, i.e. the ZnO layer, as described in Example 19, having a thickness of 30 nm. Subsequently, the active layer composed by copolymer having formula (XIa) obtained as described in Example 14 and [6,6]-phenyl-$C_{71}$-butyric acid methyl ester (P3HT:PC[71]BM), was spin-casted from a solution 1:2 (w/w) in o-xylene+1% anisaldheyde with a copolymer having formula (XIa) concentration of 24 mg/ml. The thin film was obtained by rotation at 800 rpm (acceleration 400 rpm/sec) for 90 sec. The thickness of the layer resulted to be 100 nm (measured on a test cell). The remaining layers was deposited as described in Example 19.

Figure 2:
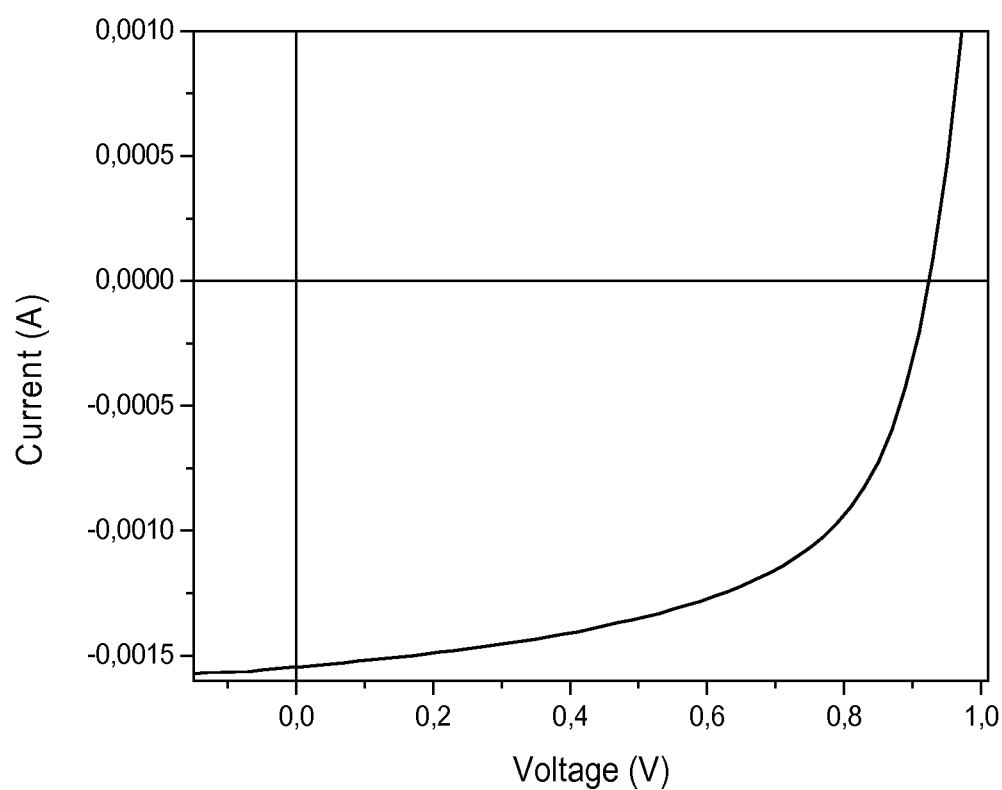
FIG. 2 shows a current-voltage curve (I-V) (Example 21)

The electrical characterization of the device was performed, in ambient atmosphere, just the device construction was terminated, operating as described in Example 19: the obtained results are given in Table 3. In FIG. 2 was reported the current-voltage curve (I-V) obtained [in abscissa was reported the voltage in volts (V); in the ordinate was reported the current in ampere (A)].

Example 22

Cell Containing Copolymer Having Formula (XIa)

Figure 5:
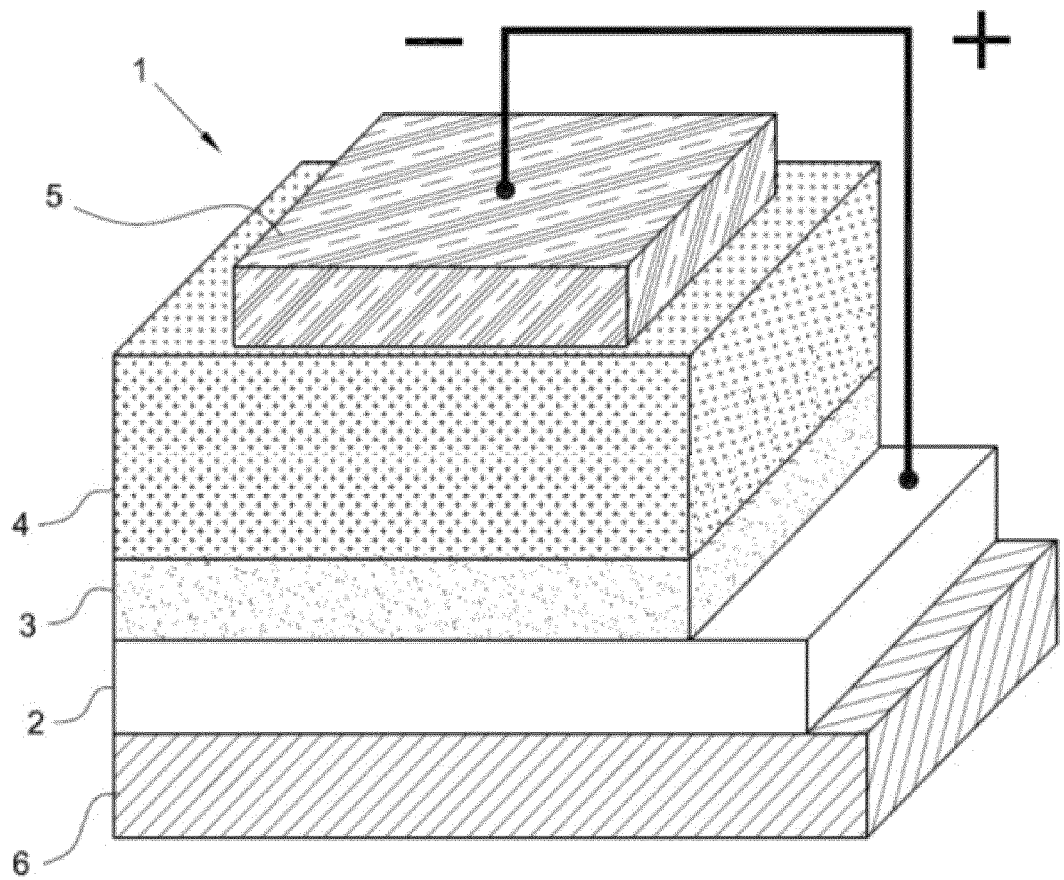
FIG. 5 shows a schematic representation of a conventional polymer solar cell (Example 22)
Figure 6:
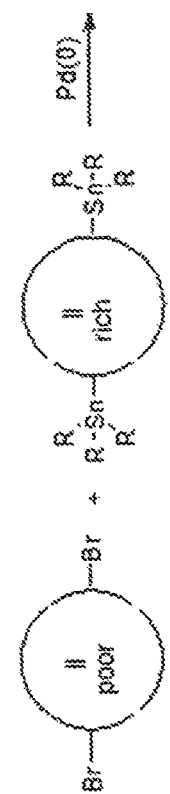
FIG. 6 shows a Stille reaction diagram in which R, which may be the same or different, represent a linear or branched $C_1$-$C_{20}$ alkyl group.
Figure 7:
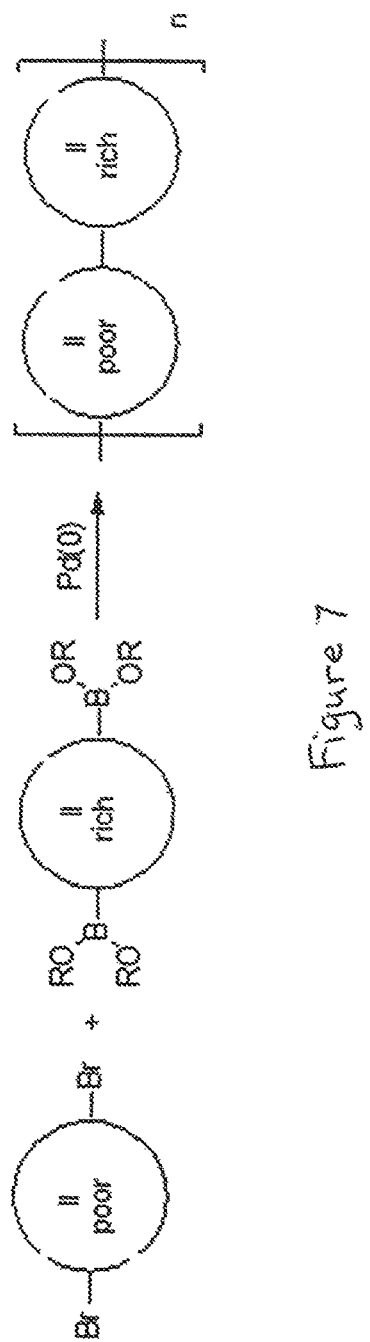
FIG. 7 shows a Suzuki reaction diagram in which R, which are the same or different, represent a hydrogen atom, or a linear or branched $C_1$-$C_{20}$ alkyl group, or the OR groups together with other atoms to which they are linked may form a heterocyclic ring having the following formula.

FIG. 5 is a schematic representation of a conventional polymer solar cell used in Example 22.

To this aim, a polymer based device was prepared on a ITO (Indium Tin Oxide) coated glass substrate (Diamond Coating Ltd.—UK). The substrate was rinsed with distilled water and then cleaned with ultrasonic treatment for 15 min in acetone and 15 min in iso-propanol. Subsequently, the solvent, was removed with compressed nitrogen and the substrate was dryed in an oven, at 110° C., overnight. Subsequently, the substrates was placed in UVO-cleaner for 25 min before the deposition of a layer of poly(3,4-ethylenedioxythiophene)poly(styrenesulfonate) (PEDOT:PSS— Clevious P VP AI 4083) by spin-coating rotating at 4000 rpm for 60 sec, at ambient temperature. The exceeding material was removed from the border of the substrate with distilled water, in order to permit the electrical connection of the ITO. The so obtained substrate was dried in an oven, at 140° C., for 10 minutes and subsequently transferred in an argon filled glove-box to complete the device structure with the deposition of the active layer and of the top electrode.

Subsequently, the active layer composed by copolymer having formula (XIa) obtained as described in Example 14 and [6,6]-phenyl-$C_{71}$-butyric acid methyl ester (P3HT:PC [71]BM), was spin-coated from a solution 1:2 (w/w) in chlorobenzene with a copolymer having formula (XIa) concentration of 20 g/l. The thin film was obtained by rotation at 800 rpm for 200 sec. The thickness of the layer resulted to be 94 nm (measured on a test cell). The thickness of the layers was measured with a profilometer Alpha step IQ (Tencor).

The polymer device structure was completed with an aluminum layer of about 80 nm, deposited by thermal evaporation in a vacuum chamber, at a pressure of $1\times10^{-6}$ mbar. The active area of the devices was 8.5 mm$^2$ and was defined by the shadow mask used for the aluminum deposition. In order to obtain a correct deposition, the ambient temperature has to be ranging from 18° C. to 21° C. and the relative humidity of the ambient has to be ranging from 3% to 45%.

Figure 3:
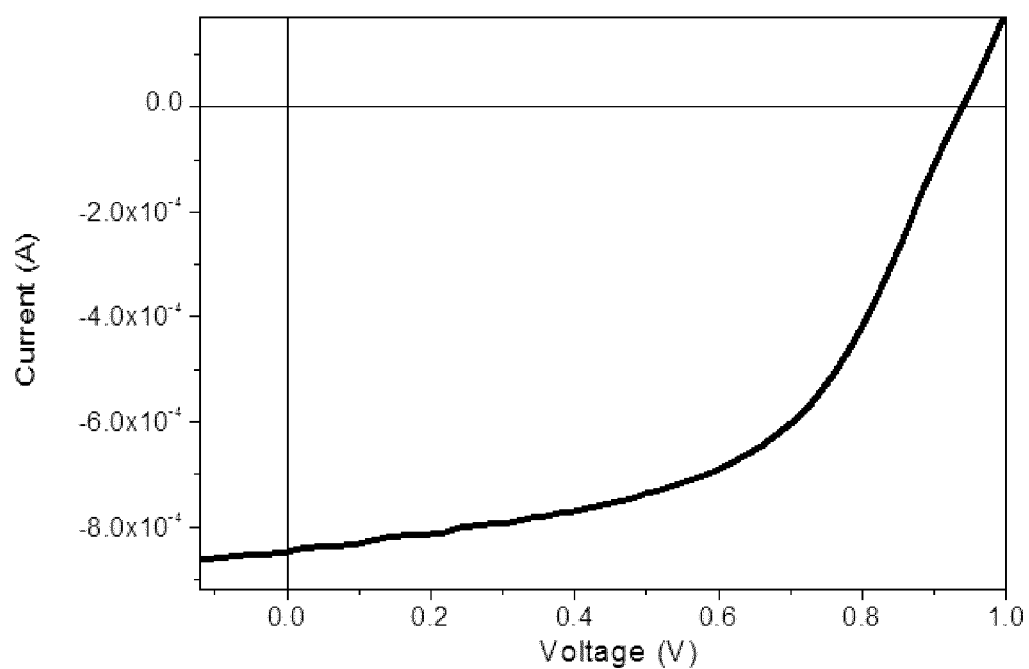
FIG. 3 shows a current-voltage curve (I-V) (Example 22)

The electrical characterization of the device was performed, in ambient atmosphere, just the device construction was terminated, operating as described in Example 19: the obtained results are given in Table 3. In FIG. 3 was reported the current-voltage curve (I-V) obtained [in abscissa was reported the voltage in volts (V); in the ordinate was reported the current in ampere (A)].

TABLE 3

| EXAMPLE[2] | FF[1] | $V_{oc}$[2] (V) | $J_{sc}$[3] (mA/cm2) | $PCE_{av}$[4] (%) |
|---|---|---|---|---|
| 19 | 0.57 | 0.56 | 10.10 | 3.30 |
| 20 | 0.50 | 0.94 | 8.10 | 3.78 |
| 21 | 0.57 | 0.92 | 9.66 | 5.07 |
| 22 | 0.55 | 0.94 | 9.99 | 5.12 |

[*]: average values;
[1]: FF (Fill Factor) defined by the following ratio:

$$\frac{V_{MPP} \cdot J_{MPP}}{V_{oc} \cdot J_{sc}}$$

wherein $V_{MPP}$ and $J_{MPP}$ are voltage and current density, respectively, corresponding to the maximum power point, $V_{oc}$ and $J_{sc}$ have the meanings reported below;
[2]: $V_{oc}$ is the open-circuit voltage;
[3]: $J_{sc}$ is the short-circuit current density;
[4]: $PCE_{av}$ is the device efficiency calculated by the following formula:

$$\frac{V_{oc} \cdot J_{sc} \cdot FF}{P_{in}}$$

wherein $V_{oc}$, $J_{sc}$ and FF have the meanings reported above and $P_{in}$ is the intensity of the light incident on the device.

The invention claimed is:
1. Polymer comprising an indacen-4-one derivative, said polymer having general formula (XI):

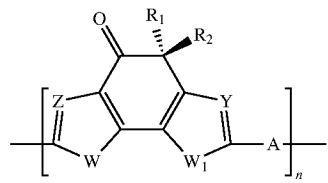

(XI)

in which:
W and W1, which are the same or different, represent an oxygen atom; a sulfur atom;
an N—$R_3$ group in which $R_3$ represents a hydrogen atom, or is selected from linear or branched $C_1$-$C_{20}$ alkyl groups;
Z and Y, which are the same or different, represent a nitrogen atom; or a C—$R_4$ group in which $R_4$ represents a hydrogen atom, or is selected from groups including linear or branched $C_1$-$C_{20}$ alkyl groups; optionally substituted cycloalkyl groups, optionally substituted aryl groups, optionally substituted heteroaryl groups, linear or branched $C_1$-$C_{20}$ alkoxyl groups, $R_5$—O—[$CH_2$—$CH_2$—O]$_n$— polyethyleneoxyl groups in which $R_5$ is selected from linear or branched $C_1$-$C_{20}$ alkyl groups, and n is an integer ranging from 1 to 4, —$R_6$—$OR_7$ groups in which $R_6$ is selected from linear or branched $C_1$-$C_{20}$ alkylene groups and $R_7$ represents a hydrogen atom or is selected from linear or branched $C_1$-$C_{20}$ alkyl groups, or is selected from groups including $R_5$—[$OCH_2$—$CH_2$-]$_n$— polyethyleneoxyl groups in which $R_5$ has the same meanings as listed above and n is an integer ranging from 1 to 4, —$COR_8$ groups in which $R_8$ is selected from linear or branched $C_1$-$C_{20}$ alkyl groups, —$COOR_9$ groups in which $R_9$ is selected from linear or branched $C_1$-$C_{20}$ alkyl groups; or represent a —CHO group, or a cyano group (—CN);
$R_1$ and $R_2$, which are the same or different, are selected from groups including linear or branched $C_1$-$C_{20}$ alkyl groups; optionally substituted cycloalkyl groups; optionally substituted aryl groups; optionally substituted heteroaryl groups; linear or branched $C_1$-$C_{20}$ alkoxyl groups; $R_5$—O—[$CH_2$—$CH_2$—O]$_n$— polyethyleneoxyl groups in which $R_5$ has the same meanings as listed above and n is an integer ranging from 1 to 4; —$R_6$—$OR_7$ groups in which $R_6$ and $R_7$ have the same meanings as listed above; —$COR_8$ groups in which $R_8$ has the same meanings as listed above; —$COOR_9$ groups in which $R_9$ has the same meanings as listed above; or represent a —CHO group, or a cyano group (—CN);
A represents an electron-acceptor group;
n is an integer ranging from 10 to 500;
wherein said electron acceptor group A is:

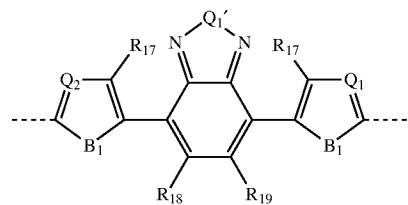

in which:
$B_1$ is a sulfur atom; an oxygen atom; a selenium atom; or an N—$R_{11}$ group in which $R_{11}$ represents hydrogen atom or is selected from linear or branched $C_1$-$C_{30}$ alkyl groups;
$Q_1$ and $Q_2$, which are the same or different, represent a nitrogen atom, a sulfur atom; an oxygen atom; a selenium atom; or a C—$R_{11}$ group in which $R_{11}$ has the same meanings as above reported;
$R_{17}$, which are the same or different, are selected from linear or branched $C_1$-$C_{20}$ alkyl groups; optionally substituted cycloalkyl groups; optionally substituted aryl groups; optionally substituted heteroaryl groups; linear or branched $C_1$-$C_{20}$ alkoxyl groups; $R_{12}$—[—$OCH_2$—$CH_2$—]$_n$— polyethyleneoxyl groups in which $R_{12}$ is selected from linear or branched $C_1$-$C_{20}$ alkyl groups and n is an integer ranging from 1 to 4; —$R_{13}$—$OR_{14}$ groups in which $R_{13}$ is selected from linear or branched $C_1$-$C_{20}$ alkylene groups and $R_{14}$ represents hydrogen atom or is selected from linear or branched $C_1$-$C_{20}$ alkyl groups; —$COR_{15}$ groups in which $R_{15}$ is selected from linear or branched $C_1$-$C_{20}$ alkyl groups, —$COOR_{16}$ groups in which $R_{16}$ is selected from linear or branched $C_1$-$C_{20}$ alkyl groups; or represent a —CHO group, or a cyano group (—CN);

$R_{18}$ and $R_{19}$, which are the same or different, represent —$R_{13}$—$OR_{14}$ groups in which $R_{13}$ and $R_{14}$ have the same meanings as above reported, —$COR_{15}$ groups in which $R_{15}$ has the same meanings as above reported; or $R_{18}$ and $R_{19}$ may optionally be linked together so as to form, together with the carbon atoms to which they are linked, a cycle or a polycyclic system containing from 3 to 14 carbon atoms, saturated, unsaturated, or aromatic, optionally containing one or more heteroatoms.

2. Photovoltaic device or solar device including a photovoltaic cell or solar cell, a photovoltaic module or solar module on either a rigid support or flexible support, comprising at least one polymer having general formula (XI) according to claim 1.

\* \* \* \* \*